United States Patent
Nelson et al.

(10) Patent No.: US 6,734,294 B2
(45) Date of Patent: May 11, 2004

(54) ISOTOPICALLY ENRICHED NUCLEIC ACIDS AND ASSOCIATED METHODS FOR THE PRODUCTION AND PURIFICATION THEREOF

(76) Inventors: Chad C. Nelson, 3246 Big Spruce Way, Park City, UT (US) 84098; Lesa M. Nelson, 3246 Big Spruce Way, Park City, UT (US) 84098

( * ) Notice: Subject to any disclaimer, the term of this patent is extended or adjusted under 35 U.S.C. 154(b) by 0 days.

(21) Appl. No.: 10/052,477

(22) Filed: Jan. 18, 2002

(65) Prior Publication Data

US 2002/0155478 A1 Oct. 24, 2002

Related U.S. Application Data

(60) Provisional application No. 60/263,263, filed on Jan. 22, 2001, and provisional application No. 60/338,525, filed on Dec. 5, 2001.

(51) Int. Cl.⁷ .................. C07H 19/00; C07H 21/02; C07H 21/04; C12Q 1/68; C12P 19/34

(52) U.S. Cl. .................. 536/22.1; 536/24.3; 536/23.1; 435/6; 435/91.2

(58) Field of Search .................. 435/6, 91.2, 375, 435/91.31, 69.1; 536/27.3, 28.1, 26.13, 24.5; 514/44

(56) References Cited

U.S. PATENT DOCUMENTS 5,872,241 A  * 2/1999 Pyle et al. .................. 536/24.5

OTHER PUBLICATIONS

SantaLucia et al. "Synthesis and NMR of RNA with selective isotopic enrichment in the bases" Nucleic Acids Research, 1995, vol. 23, No. 23 pp. 4913–4921.*
Coleman et al., "Practical Aspects of Stable Isotope Mass Spectrometry" Jul. 22, 1997.*
Louis et al "Preparation of Uniformly Isotope–labeled DNA Oligonucleotides for NMR Spectroscopy" The Journal of Biological Chemistry vol. 273, No. 4, Jan. 23, 1998, pp. 2374–2378.*
Batey R.T. et al., *Improved Large Scale Culture of Methylophilus Methylotrophus for $^{13}C/^{15}N$ Labeling and Random Fractional Deuteration of Ribonucleotides*, Nucleic Acids Researchvol. 24, No. 23, pp. 4859–4860, 1996.
Berkenkamp S., et al., *Infrared MALDI Mass Spectrometry of Large Nucleic Acids*, Science, vol. 281, pp. 260–262, 1998.
Carr S.A. and Burlingame A.L., *The Meaning and Usage of the Terms Monoisotopic Mass, Average Mass, Mass Resolution, and Mass Accuracy for Measurements of Biomolecules*, Sciences, Humana Press, Inc., Append. XI, pp. 546–553, 1996.

Chen X. et al., *Stable–Isotope–Assisted MALDI–TOF Mass Spectrometry for Accurate Determination of Nucleotide Compositions of PCR Products*, Anal. Chem., vol. 71, No. 15, pp. 3118–3125, 1999.
Chen X. et al., *A PCR–Based Method for Uniform $^{13}C/^{15}N$ Labeling of Long DNA Oligomers*, FEBS Letter, pp. 372–376, 1998.
Griffin T.J. and Smith L.M., *Single–Nucleotide Polymorphism Analysis by MALDI–TOF Mass Spectrometry*, Trends Biotechnol., vol. 18, pp. 77–84, 2000.
Krahmer M.T. et al., *Electrospray Quadrupole Mass Spectrometry Analysis of Model Oligonucleotides and Polymerase Chain Reaction Products: Determination of Base Substitutions, Nucleotide Additions/Deletions, and Chemical Modifications*, Anal. Chem., vol. 71, No. 14, pp. 2893–2900, 1999.
Krahmer M.T. et al., *MS for Identification of Single Nucleotide Polymorphisms and MS/MS for Discrimination of Isomeric PCR Products*, Anal. Chem., vol. 72, No. 17, pp. 4033–4040, 2000.
Larsen B. et al., *Nonlinearity in Genetic Decoding: Homologous DNA Replicase Genes Use Alternatives of Transcriptional Slippage or Translational Frameshifting*, PNAS, vol. 97, No. 4, pp. 1683–1688, 2000.
Liu C. et al., *On–Line Microdialysis Sample Cleanup for Electrospray Ionization Mass Spectrometry of Nucleic Acid Samples*, Anal. Chem., vol. 68, No. 18, pp. 3295–3299, 1996.
Louis J.M. et al., *Preparation of Uniformly Isotope–Labeled DNA Oligonucleotides for NMR Spectroscopy*, J. Biol. Chem., vol. 273, No. 4, pp. 2374–2378, 1998.
Marshall, A.G. et al., *Protein Molecular Mass to 1 Da by $^{13}C$, $^{15}N$ Double–Depletion and FT–ICR Mass Spectrometry*, J. Am. Chem. Soc., vol. 119, No. 2, pp. 433–434, 1997.
McCloskey J.A., *Mass Spectrometry*, Methods in Enzymology, Academic Press, Inc., vol. 193, pp. 882–886, 1990.
Muddiman D.C., et al., *Characterization of PCR Products From Bacilli Using Electrospray Ionization FTICR Mass Spectrometry*, Anal. Chem., vol. 68, No. 21, pp. 3705–3712, 1996.
O'Connor P.B., et al., *Isotopic Assignment in Large–Molecule Mass Spectra by Fragmentation of a Selected Isotopic Peak*, Anal. Chem., vol. 68, No. 3, pp. 542–545, 1996.
Pomerantz S.C. and McCloskey J.A., *Fractional Mass Values of Large Molecules*, Org. Mass Spectrom., vol. 22, pp. 251–253, 1987.
Rockwood A.L. et al., *Rapid Calculation of Isotope Distributions*, Anal. Chem., vol. 67, No. 15, pp. 2699–2704, 1995.

(List continued on next page.)

Primary Examiner—Ethan Whisenant
(74) Attorney, Agent, or Firm—Workman Nydegger

(57) ABSTRACT

The present invention relates to isotopically enriched nucleic acids and methods for their production and purification. The invention further relates to methods for the use of said nucleic acids in analysis with mass spectrometry. Use of isotopically enriched nucleic acids in creating second generation products is also provided.

72 Claims, 6 Drawing Sheets

OTHER PUBLICATIONS

Yergey, J.A., *A General Approach to Calculating Isotopic Distributions for Mass Spectrometry*, Intl. J. Mass Spectrom. Ion Phys., vol. 52, pp. 337–349, 1983.

Zimmer D.P. and Crothers D.M., *NMR of Enzymatically Synthesized Uniformly $^{13}C^{15}N$–Labeled DNA Oligonucleotides*, Proc. Natl. Acad. Sci., vol. 92, pp. 3091–3095, 1995.

Zubarev R.A. et al., *Approaches and Limits for Accurate Mass Characterization of Large Biomolecules*, Anal. Chem., vol. 67, No. 20, pp. 3793–3798, 1995.

* cited by examiner

US 6,734,294 B2

ISOTOPICALLY ENRICHED NUCLEIC ACIDS AND ASSOCIATED METHODS FOR THE PRODUCTION AND PURIFICATION THEREOF

RELATED APPLICATIONS

This application claims priority to, and the benefit of, U.S. provisional patent application serial Nos. 60/263,263, filed Jan. 22, 2001 and 60/338,525, filed Dec. 5, 2001, which are hereby incorporated by reference in their entirety.

FIELD OF THE INVENTION

The present invention relates generally to isotopically enriched nucleic acids, and methods for the production and purification thereof. More particularly, the present invention relates to isotopically enriched nucleic acids, and methods for the production and purification thereof for use in analysis with mass spectrometry.

BACKGROUND OF THE INVENTION

Mass spectrometry is a well-known and widely used tool for analyzing and identifying chemical compositions. Electrospray ionization (ESI) mass spectrometry and matrix-assisted laser desorption ionization (MALDI) mass spectrometry have been used to analyze, with varying degrees of sensitivity, a wide variety of materials including large chemical entities, e.g. biomolecules. Sufficient spectrometric sensitivity and resolution of many large molecules, especially nucleic acids and proteins, has proven difficult for a variety of reasons. One such difficulty arises from the existence of different naturally occurring isotopes for chemical elements contained therein, especially for carbon (C), nitrogen (N), and oxygen (O). For large biomolecules, the statistical distribution of naturally-occurring isotopes results in a mass spectrum with broad peak widths, in which small differences in mass are difficult to resolve. This problem is compounded with increasing size of the molecule.

Attempts to prepare biomolecules compatible with mass spectrometry analysis continue to be sought through on-going research and development efforts.

SUMMARY OF THE INVENTION

The present invention is directed to nucleic acids isotopically enriched in an isotope of oxygen. Another aspect of the invention relates to methods for the production and purification of such isotopically enriched nucleic acids. Another aspect of the invention relates to methods for the use of said nucleic acids in mass spectrometric analysis. In still another aspect of the invention, the use of isotopically enriched nucleic acids to create second generation products, such as their use in polymerase chain reactions (PCRs) is described.

One aspect of the invention relates to nucleotides and oligonucleotides, wherein said nucleotides and oligonucleotides are isotopically enriched in one of the isotopes of oxygen. Another aspect of the invention relates to nucleotides and oligonucleotides, wherein said nucleotides and oligonucleotides are isotopically enriched in one or more of the constituent chemical elemental isotopes selected from the group consisting of oxygen (O); oxygen and carbon (C); and oxygen, carbon, and nitrogen (N). Another aspect of the invention relates to nucleotides and oligonucleotides, wherein said nucleotides and oligonucleotides are isotopically enriched in one or more of the constituent chemical elemental isotopes selected from the group consisting of $^{16}O$ and $^{12}C$; and $^{12}C$, $^{14}N$ and $^{16}O$. Nucleotides and oligonucleotides of the invention which are enriched in oxygen may also be enriched in other isotopes of chemical elements such as $^{12}C$ and $^{15}N$. Another aspect of the invention is a method for the preparation of a nucleotide that is isotopically enriched in one or more of the constituent chemical elemental isotopes selected from the group consisting of $^{16}O$; $^{16}O$ and $^{12}C$; and $^{12}C$, $^{16}O$ and $^{14}N$, the method comprising the steps of: (a) producing DNA or RNA in an organism grown in a growth medium in which the nutrients, reagents and solvents are isotopically enriched in one or more of the constituent chemical elemental isotopes selected from the group consisting of $^{16}O$; $^{16}O$ and $^{12}C$; and $^{12}C$, $^{14}N$ and $^{16}O$; (b) isolating the isotopically enriched DNA or RNA; (c) hydrolyzing the isotopically enriched DNA or RNA in $^{16}O$ enriched water. In one aspect, the nucleotide is enriched in an isotope of oxygen.

Another aspect of the invention is a method for determining the mass of an oligonucleotide that is isotopically enriched in one or more of the constituent chemical elemental isotopes selected from the group consisting of $^{16}O$; $^{16}O$ and $^{12}C$; and $^{12}C$, $^{14}N$ and $^{16}O$, the method comprising the steps of: (a) making an oligonucleotide isotopically enriched in one or more of the constituent chemical elemental isotopes selected from the group consisting of $^{16}O$; $^{16}O$ and $^{12}C$; and $^{12}C$, $^{14}N$ and $^{16}O$; (b) determining the mass of the isotopically enriched DNA or RNA using mass spectrometry. In one aspect, the oligonucleotide is enriched in an isotope of oxygen.

Other features of the present invention will become clearer from the following detailed description of the invention, taken with the accompanying drawings and claims.

The entire disclosures of the publications and references referred to in this specification are incorporated herein by reference in their entirety.

BRIEF DESCRIPTION OF THE FIGURES

in FIG. 3B each DNA molecule is isotopically enriched to greater than 99.90 atom % in $^{12}C$, $^{16}O$, and $^{14}N$.

in FIG. 4B each DNA molecule is isotopically enriched to greater than 99.90 atom % in $^{12}C$, $^{16}O$ and $^{14}N$. Only antisense strands are shown in the figure.

in FIG. 5B each DNA molecule is isotopically enriched to greater than 99.90 atom % in $^{12}$C, $^{16}$O and $^{14}$N.

in FIG. 6B, each DNA molecule is isotopically enriched to greater than 99.90 atom % in $^{12}$C, $^{16}$O and $^{14}$N.

DETAILED DESCRIPTION OF THE INVENTION

Figure 1:
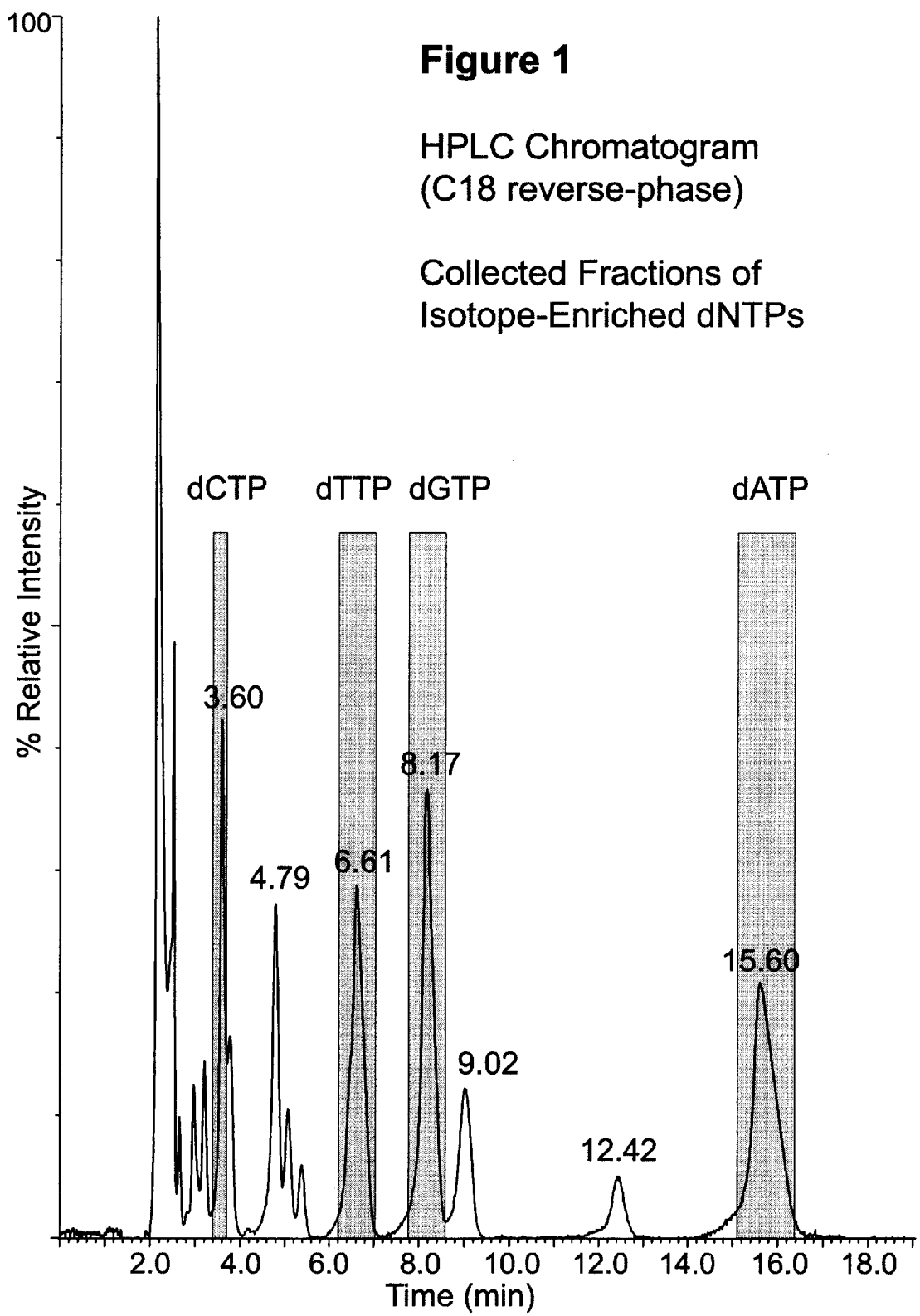
FIG. 1 is an HPLC chromatogram of triphosphorylated deoxynucleotides (dNTP's) in which the nucleoside and alpha phosphate moieties are isotopically enriched to greater than 99.90 atom % in $^{12}C$, $^{16}O$, and $^{14}N$.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

In accordance with the present invention and as used herein, the following terms are defined with the following meanings, unless explicitly stated otherwise.

The term "biomolecule" refers to DNA, RNA (including mRNA, rRNA, tRNA and tmRNA), nucleotides and nucleosides.

The term "nucleic acid" may refer either to a molecule of DNA of indeterminate length or to a molecule of RNA of indeterminate length. In some aspects of the invention biomolecules and/or nucleic acids may be produced using a variety of known techniques, such as polymerase chain reaction (PCR) amplification, reverse-transcriptase polymerase chain reaction (RT-PCR) amplification, oligo ligation amplification (OLA), rolling-circle amplification, or single nucleotide primer extension reaction (SNuPE). Such techniques are well known to one skilled in the art and further are described in laboratory manuals such as Sambrook et al, ("Molecular Cloning: A Laboratory Manual", Third edition, Cold Spring Harbor Laboratory, 2001) or Ausubel et al. ("Current Protocols in Molecular Biology", John Wiley & Sons, 1998) both of which are incorporated herein by reference in their entirety, including any drawings, figures or tables.

The term "nucleic acid structural modification" refers to any structural change to a nucleic acid. This includes any structural alteration of any moiety of bases such as adenine, guanine, uracil, cytosine, thymine and xanthine, as well as nucleosides of the bases such as adenosine, guanosine, uridine, cytidine, thymidine, and xanthosine, as well as other bases and nucleosides such as may be found in tRNA molecules. This term refers both to polymers of such nucleotides, such as DNA and RNA, as well as the single bases, nucleosides and nucleotides. "Nucleic acid structural modifications" may refer to any post-transcriptional or post-synthetic modifications, naturally-occurring derivatives, or cellular chemistries or reactions that result in a molecular structural change that modifies the base, nucleoside, or nucleotide moieties of a nucleic acid. "Nucleic acid structural modifications" include, but are not limited to, those selected from the group consisting of alkylations, methylations, thiolations, oxidations, peptide derivatizations, sugar derivatizations, and radiation-induced or radical-induced reactions of nucleic acid bases, nucleosides, or nucleotides. Examples of such nucleic acid structural modifications are found in naturally occurring tRNA molecules and include such modifications as 2'-O-methyl-cytidine, N6-methyl-adenosine, 4-thio-uridine, and pseudo-uridine. Further examples of nucleic acid structural modifications can be found in can be found in McCloskey, *Methods Enzymol* 1990;193:771–81; Crain and McCloskey, *Nucleic Acids Res.* 1996;24(1):98–9; Limbach et al., *Biochimie* 1995;77(1–2):135–8; Limbach et al., *Nucleic Acids Res.* 199;22(12):2183–96; McCloskey et al., *Nucleic Acids Res.* 2001;29(22):4699–706; Rozenski et al., *Nucleic Acids Res.* 1999;27(1):196–7; Crain and McCloskey, *Curr Opin Biotechnol.* 1998;9(1):25–34; Felden et al., *EMBO J.* 1998;17(11):3188–96; and Noon et al., *J Bacteriol.* 1998;180(11):2883–88, along with online databases referenced therein; these references are hereby incorporated herein in their entirety, including any figures, tables or drawings. "Nucleic acid structural modifications" may also include modifications to the backbone of nucleic acids such as phosphothioate backbones, peptide nucleic acid backbones or other modified backbones.

The phrase "chemical element" refers to an atom, such as, for example, carbon, oxygen, phosphorus, nitrogen or hydrogen.

The phrase "chemical elemental isotope" refers to an isotope of a chemical element. For example, $^{12}$C and $^{13}$C are both chemical elemental isotopes of carbon.

The "natural abundance" of a chemical elemental isotope refers to the average terrestrial abundance of stable isotopes of that chemical element. For example, the natural abundance of $^{12}$C is 98.9 atom %; the natural abundance of $^{14}$N is 99.63 atom %; the natural abundance of $^{16}$O is 99.76 atom %; the natural abundance of $^{17}$O is 0.037 atom %; the natural abundance of $^{18}$O is 0.204 atom %

The "predominant chemical elemental isotope" is the stable chemical elemental isotope that is most abundant in the naturally abundant isotopic distribution of a chemical element.

The phrase "isotopically enriched," refers to an increased purity of a chemical elemental isotope relative to the natural abundance of that isotope for one or more constituent atoms. In one embodiment of the invention, isotopic enrichment refers to increasing the purity above 99.90 atom % of one of the isotopes of oxygen, selected from the group of $_{16}$O, $^{17}$O and $^{18}$O. In another embodiment, isotopic enrichment refers to increasing the purity of $^{16}$O above 99.90 atom %. In another embodiment of the invention, isotopic enrichment refers to increasing the purity of $^{12}$C and $^{16}$O above 99.90 atom % or the purity of $^{14}$N, $^{12}$C, and $^{16}$O above 99.90 atom %. In yet another embodiment, the isotopic enrichment of $^{16}$O; $^{12}$C and $^{16}$O; or $^{12}$C, $^{14}$N, and $^{16}$O is between about 99.90 atom % and about 99.99 atom %. In other embodiments, the isotopic enrichment of $^{16}$O; $^{12}$C and $^{16}$O; or $^{12}$C, $^{14}$N, and $^{16}$O is between about 99.91 atom %, 99.93 atom %, and 99.95 atom % on the lower end and about 99.93 atom %, 99.95 atom %, 99.98 atom % and 99.99 atom % on the upper end. In another embodiment, biomolecules enriched in $^{16}$O are further enriched in one or more chemical elemental isotopes selected from the group consisting of $^{13}$C; $^{15}$N; and $^{13}$C and $^{15}$N.

The term "purity" refers to the degree to which one chemical element isotope is free from being mixed with other isotopes of the same chemical element. The term purity does not require absolute (100 atom %) purity. For example, naturally occurring $^{12}C$ is present at 98.9 atom % purity.

The term "constituent" refers to that which is a part or component of a whole. For example, carbon is a constituent chemical element of adenosine.

The phrase "nucleoside kinasing enzyme" refers to an enzyme that catalyzes or facilitates the phosphorylation of nucleosides or nucleotides. Such enzymes include, without limitation, pyruvate kinase, guanylate kinase, nucleoside monophosphate kinase, myokinase, thymidylate kinase, various *Escherichia coli* (*E. coli*) kinasing enzyme fractions, and mixtures thereof.

For the purposes of this invention, the term "microorganism" refers to any microorganism which may be grown using a growth media, and from which oligonucleotides may be harvested. Examples of microorganisms useful in the present invention include without limitation, bacteria, fungi, microalgae, protozoa, as well as mixtures thereof. Typically *E. coli* is employed as the microorganism. In one embodiment, the growth medium is a minimal growth medium.

For the purposes of this invention, the term "organism" refers to microorganisms and also other organisms, as well as cells derived from other organisms. In one embodiment, the term "organism" includes tissue culture cells derived from organisms such as insects and mammals.

The term "grown" when used in reference to a microorganism or organism refers to increasing cell number and cell mass in a controlled growth environment. The growth media may be liquid or solid. The growth conditions may be either aerobic or anaerobic.

A "methylation deficient" microorganism refers to a microorganism that contains a relatively low amount of methylated nucleotides in its DNA compared to wild type *E. coli*. Examples of a methylation deficient microorganism include specific strains of *E. coli* that contain lam(-) and/or dam(-) mutations.

The terms "minimal growth media" and "growth medium" refer to media that provide the nutrients, salts, water and atmosphere needed by an organism for growth. Such media typically include a carbon source, including glucose or methanol; a nitrogen source, including ammonium salts; an oxygen source, including sulfates, phosphates and aerobic oxygen; sulfur and phosphorus sources, including sulfates or phosphates; and inorganic salts, including sodium, potassium, calcium, magnesium and chloride salts. Growth media for tissue culture may also include additional components, such as growth factors.

The term "nutrient" refers to any substance that can be metabolized by an organism to provide energy and/or components for synthesis of cellular components and for cell growth and generation.

The term "reagents" refers to a chemical agent for use in chemical reactions. The chemical reactions may be in vitro or in vivo. When used in connection with growth media, the term "reagents" includes those constituents other than nutrients, such as inorganic salts, and the term also includes the oxygen atoms present in the water and atmosphere supplied with the growth media.

As used herein, "nucleoside" refers to a compound containing a purine base (e.g. adenine and guanine) or a pyrimidine base (e.g. cytosine, thymine, and uracil) linked to either d or l forms of ribose or deoxyribose or derivatives thereof, whether occurring naturally or produced synthetically.

As used herein, "nucleotide" refers to a 5' phosphate ester of a nucleoside. A nucleotide may be either a ribonucleotide (i.e. phosphate ester of a d-ribose containing nucleoside), or a deoxyribonucleotide (i.e. phosphate ester of a d-deoxyribose containing nucleoside). Further, nucleotides may contain one, two or three phosphate moieties (monophosphate, diphosphate, or triphosphate, respectively). Deoxyribonucleoside monophosphates are commonly abbreviated as follows: dAMP (deoxyadenosine monophosphate), dGMP (deoxyguanosine monophosphate), dCMP (deoxycytidine monophosphate) and dTMP (deoxythymidine monophosphate). Ribonucleoside monophosphates are commonly abbreviated as follows: AMP (adenosine monophosphate), GMP (guanosine monophosphate), CMP (cytidine monophosphate) and UMP (uridine monophosphate). Deoxyribonucleoside triphosphates are commonly abbreviated as follows: dATP (deoxyadenosine triphosphate), dGTP (deoxyguanosine triphosphate), dCTP (deoxycytidine triphosphate) and dTTP (deoxythymidine triphosphate). Ribonucleoside triphosphates are commonly abbreviated as follows: ATP (adenosine triphosphate), GTP (guanosine triphosphate), CTP (cytidine triphosphate) and UTP (uridine triphosphate). Nucleotides are well known to those skilled in the art as the building blocks of DNA or RNA, depending on the type of ribose present.

The term "oligonucleotide" refers to a chain of nucleotides which may contain between about 50 and about 2000 nucleotides. Such a term also refers to all forms of DNA and all forms of RNA. The term "oligonucleotide" may include chains which are at least as long as 50, 70, 80, 100, 120, 150, 175, and 200 nucleotides. These chains maybe up to 2000, 1500, 1000, 800, 600, 500, 450, 400, 350, 300, 250, 200, 175, 150, 125 and 100 nucleotides in length. Thus, for example, the oligonucleotides may be between 150 and 600 nucleotides in length.

The term "isolating" refers to separating (a substance) in pure form from a combined mixture, wherein pure form comprises about 90% or higher purity.

The term "hydrolyze" refers to a chemical reaction in which a covalent bond of an oligonucleotide or other nucleic acid (DNA or RNA) is broken and the components of a molecule of water are incorporated at the site of the broken bond, adding —H and —OH in the process. Such a reaction may produce, for example, nucleotides or nucleosides. Such a reaction may occur in the presence of an enzyme, such as, for example, P1 endonuclease. In one embodiment of the invention, $^{16}O$-enriched water is employed in hydrolysis reactions.

The terms "alpha phosphate," "beta phosphate," and "gamma phosphate" refer to the three phosphate groups contained in a nucleoside triphosphate. The alpha ($\alpha$) phosphate is the phosphate group attached directly to the sugar moiety, the beta ($\beta$) phosphate is the phosphate group attached to the alpha phosphate, and the gamma ($\gamma$) phosphate is the phosphate group attached to the beta phosphate.

The inventors have found that isotopic enrichment of oxygen can increase the ability to resolve large oligonucleotides, as analyzed by mass spectrometry, as compared to nucleic acids containing the natural isotopic abundance of oxygen. The ability to resolve large oligonucleotides is also increased by isotopic enrichment of other constituent chemical elements such as, for example, carbon and nitrogen. The narrower distribution of possible isotopic compositions for molecular ions creates narrower mass spectrometric peak widths thus improving the ability to resolve large oligonucleotides. As the isotopic purity increases above 99.9 atom %, for example to 99.93 atom % or 99.95 atom %, the length of the oligonucleotide that can be successfully resolved with mass spectrometry increases. Since the total-ion signal of the molecular ions are 'funneled' into a narrower isotopic distribution and, thus, narrower peak width, there is a concomitant increase in the relative peak intensity or peak height. As a result of the narrower peak width and increased peak intensity, the present invention increases the ability to resolve DNA or RNA sequences. The present invention can be used to detect genetic changes such as, for example, single nucleotide substitution polymorphisms (SNPs), nucleotide deletions, nucleotide insertions, and variations in short tandem repeats (STRs).

Analyses which can benefit from isotopic enrichment of nucleic acids include without limitation, oligonucleotide composition analysis, identification of previously unknown mutations or genetic variants, sequence validation, and sequence comparison, as well as mutation screening in any gene, any region of DNA or genomic DNA, genotyping for linkage analysis, and clinical genetic diagnostic testing for detection of known or unknown mutations associated with disease. In addition, isotopic enrichment benefits analysis of all forms of RNA molecules, especially RNA with structural modifications, such as tRNA. Small mass changes (e.g. SNPs) may be readily detected in large nucleic acids, including oligonucleotides of about 150 nucleotides or more, using mass spectrometric analysis.

One aspect of the invention is a nucleoside monophosphate compound wherein the compound is isotopically enriched in one of the isotopes of oxygen. In another embodiment the nucleoside monophosphate compound is isotopically enriched in one or more of the constituent chemical elemental isotopes selected from the group consisting of $^{16}O$; $^{12}C$ and $^{16}O$; and $^{12}C$, $^{14}N$ and $^{16}O$. In another embodiment the nucleoside monophosphate compound is isotopically enriched in $^{16}O$. In yet another embodiment the nucleoside monophosphate compound is isotopically enriched in $^{12}C$, $^{14}N$, and $^{16}O$. Yet another embodiment is a nucleoside monophosphate compound wherein the compound is isotopically enriched in $^{16}O$ as well as in one or more constituent chemical elemental isotopes selected from the group consisting of $^{13}C$; $^{15}N$; and $^{13}C$ and $^{15}N$. In one embodiment of the invention, each isotopically enriched chemical element comprised in the nucleoside monophosphate is isotopically enriched to between about 99.90 atom % and about 99.99 atom % purity. In another embodiment of the invention, each isotopically enriched chemical element comprised in the nucleoside monophosphate is isotopically enriched to between about 99.91 atom % and about 99.95 atom % purity. In another embodiment, each isotopically enriched chemical element comprised in the nucleoside monophosphate is isotopically enriched to at least 99.9 atom % purity. In yet another embodiment, each isotopically enriched chemical element comprised in the nucleoside monophosphate is isotopically enriched to at least about 99.93 atom % purity. In yet another embodiment, each isotopically enriched chemical element comprised in the nucleoside monophosphate is isotopically enriched to at least 99.93 atom % purity. In another embodiment, each isotopically enriched chemical element comprised in the nucleoside monophosphate is isotopically enriched to at least about 99.95 atom % purity. In another embodiment, each isotopically enriched chemical element comprised in the nucleoside monophosphate is isotopically enriched to at least about 99.99 atom % purity.

One aspect of the invention is a nucleoside triphosphate compound wherein the nucleoside and alpha phosphate moieties are isotopically enriched in one of the isotopes of oxygen. One embodiment is a nucleoside triphosphate compound wherein the nucleoside and alpha phosphate moieties are isotopically enriched in one or more of the constituent chemical elemental isotopes selected from the group consisting of $^{16}O$; $^{12}C$ and $^{16}O$ and $^{12}C$, $^{14}N$ and $^{16}O$. One embodiment is a nucleoside triphosphate compound wherein the nucleoside and alpha phosphate moieties are isotopically enriched in $^{16}O$. Another embodiment is a nucleoside triphosphate compound wherein the nucleoside and alpha phosphate moieties are isotopically enriched in the constituent chemical elemental isotopes $^{12}C$, $^{14}N$, and $^{16}O$. Another aspect is a nucleoside triphosphate compound wherein the compound is isotopically enriched in $^{16}O$ as well as in one or more constituent chemical elemental isotopes selected from the group consisting of $^{13}C$; $^{15}N$; and $^{13}C$ and $^{15}N$, wherein the compound comprises beta and gamma phosphate groups that are not isotopically enriched. In another embodiment, the beta and gamma phosphate groups are isotopically enriched. In one embodiment of the invention, each isotopically enriched chemical element comprised in the nucleoside triphosphate is isotopically enriched to between about 99.90 atom % and about 99.99 atom % purity. In another embodiment of the invention, each isotopically enriched chemical element comprised in the nucleoside triphosphate is isotopically enriched to between about 99.91 atom % and about 99.95 atom % purity. In another embodiment, each isotopically enriched chemical element comprised in the nucleoside triphosphate is isotopically enriched to at least 99.9 atom % purity. In yet another embodiment, each isotopically enriched chemical element comprised in the nucleoside triphosphate is isotopically enriched to at least about 99.93 atom % purity. In another embodiment, each isotopically enriched chemical element comprised in the nucleoside triphosphate is isotopically enriched to at least about 99.95 atom % purity. In another embodiment, each isotopically enriched chemical element comprised in the nucleoside triphosphate is isotopically enriched to at least about 99.99 atom % purity.

One aspect of the invention is isotopically enriched RNA or DNA wherein the RNA or DNA is isotopically enriched in one of the isotopes of oxygen. One embodiment of the invention is isotopically enriched RNA or DNA wherein the RNA or DNA is isotopically enriched in one or more of the constituent chemical elemental isotopes selected from the group consisting of $^{16}O$; $^{12}C$ and $^{16}O$; and $^{12}C$, $^{14}N$ and $^{16}O$. In one embodiment, the DNA or RNA is isotopically enriched in $^{16}O$. In another embodiment of the invention the RNA or DNA is isotopically enriched in the constituent chemical elemental isotopes $^{12}C$, $^{16}O$ and $^{14}N$. In another embodiment the DNA or RNA is isotopically enriched in $^{16}O$ as well as in one or more constituent chemical elemental isotopes selected from the group consisting of $^{13}C$; $^{15}N$; and $^{13}C$ and $^{15}N$. In one embodiment of the invention, each isotopically enriched chemical element comprised in RNA or DNA is isotopically enriched to between about 99.90 atom % and about 99.99 atom % purity. In another embodiment of the invention, each isotopically enriched chemical element comprised in RNA or DNA is isotopically enriched to between about 99.91 atom % and about 99.95 atom % purity. In one embodiment of the invention, each isotopically enriched chemical element comprised in RNA or DNA is isotopically enriched to at least 99.9 atom % purity. In another embodiment, each isotopically enriched chemical element comprised in RNA or DNA is isotopically enriched to at least 99.93 atom % purity. In another embodiment, each isotopically enriched chemical element comprised in RNA or DNA is isotopically enriched to at least 99.95 atom % purity. In yet another embodiment, each isotopically enriched chemical element comprised in RNA or DNA is isotopically enriched to at least 99.99 atom % purity.

According to one aspect of the present invention, a method of making isotopically enriched nucleic acids includes the steps of providing an organism growth media containing isotopically enriched components, growing the organism using the media, and harvesting isotopically enriched nucleic acids from the organism.

A wide variety of typical growth media, which may be used for growing organisms, are known to those skilled in the art of microbiology and molecular biology. Specific media ingredients may be dictated according to the particular organism to be cultured and formulated using the knowledge of one of ordinary skill in the art. However, in one aspect, the media may be serum free. In another aspect, the media may be free from animal products, such as, for example animal proteins and animal lipids. In one embodiment of the invention, the media comprises salts of ammonium, potassium, magnesium, calcium, sulfate, chloride, and phosphate ions, as well as glucose.

The nutrients, reagents and solvents used to prepare the growth media may be completely isotopically enriched or selectively isotopically enriched, as required in order to achieve a specific result. Any component of the media which comprises a chemical element that is targeted for isotopic enrichment should contain that chemical element in at least about 99.9 atom % isotopic purity. A variety of isotopically enriched compounds, including many of those recited herein may be obtained from various commercial sources, such as Isotec, Inc., (Miamisburg, Ohio). Reagents not containing chemical elements targeted for isotopic enrichment should be at least about 99.95 atom % pure to decrease chance or trace-level contamination from impurities that may contain natural isotope abundances of the targeted chemical element, such as, for example oxygen, carbon, and nitrogen. In one embodiment of the invention, cell growth is performed in at least about 99.98 atom % pure $^{16}O_2$. In this embodiment, the $^{16}O_2$ atmosphere is maintained or purged within the environment or flask containing the cells and growth media. In another embodiment, the methods described herein further include precautions to reduce exposure to water not isotopically enriched in $^{16}O$ (non-$^{16}O$ enriched water). For example, the glassware used can be heated and dried to remove excess water. Dry atmospheres can also be used. In another embodiment, cell growth is performed in at least about 99.98 atom % pure $^{17}O_2$ and the methods described herein include precautions to reduce exposure to water not isotopically enriched in $^{17}O$ ($^{17}O$ enriched water). In another embodiment, cell growth is performed in at least about 99.98 atom % pure $^{18}O_2$ and the methods described herein include precautions to reduce exposure to water not isotopically enriched in $^{18}O$ ($^{18}O$ enriched water).

Naturally-occurring isotopes of hydrogen and phosphorus are employed in the current invention. The element of hydrogen is incorporated in all products throughout the invention as the naturally-occurring isotopes of hydrogen (i.e. not isotopically enriched), since the $^1H$ isotope has a natural abundance of 99.985 atom % purity. Further isotopic enrichment of this element is relatively insignificant in terms of benefit, compared to the other elements (e.g. C, N, and O). Moreover, the use of $^2H$ or other hydrogen isotopes is not considered practical, due to stability of incorporation owing to rates of hydrogen-exchange events and complexities associated with hydrogen-migration properties. The element of phosphorous exists as a single stable isotope (i.e. $^{31}P$ has a natural abundance of 100 atom % purity).

It has been found that when components comprising isotopically enriched chemical elements are incorporated into the growth media, the nucleic acids harvested from an organism grown thereon also contain isotopically enriched chemical elements. Such nucleic acids, including both RNA and DNA, may be analyzed using mass spectrometry as harvested.

One aspect of the invention is a method for the preparation of RNA or DNA in which the RNA or DNA is isotopically enriched in one of the isotopes of oxygen, the method comprising the steps of: (a) producing RNA or DNA in an organism grown in a growth medium in which the nutrients, reagents and solvents are isotopically enriched in the same isotope of oxygen; (b) isolating isotopically enriched RNA or DNA. One embodiment of the invention is a method for the preparation of RNA or DNA in which the RNA or DNA is isotopically enriched in one or more of the constituent chemical elemental isotopes selected from the group consisting of $^{16}O$; $^{16}O$ and $^{12}C$, and $^{12}C$, $^{14}N$ and $^{16}O$, the method comprising the steps of: (a) producing RNA or DNA in an organism grown in a growth medium in which the nutrients, reagents and solvents are isotopically enriched in one or more of the constituent chemical elemental isotopes selected from the group consisting of $^{16}O$; $^{16}O$ and $^{12}C$, and $^{12}C$, $^{14}N$ and $^{16}O$; (b) isolating isotopically enriched RNA or DNA. In one embodiment, the DNA or RNA and the nutrients, reagents and solvents of the growth medium are isotopically enriched in $^{16}O$. In another embodiment, the DNA or RNA and the nutrients, reagents and solvents of the growth medium are isotopically enriched in $^{12}C$, $^{14}N$ and $^{16}O$. In yet another embodiment, the DNA or RNA and the nutrients, reagents and solvents of the growth medium are isotopically enriched in $^{16}O$ as well as in one or more constituent chemical elemental isotopes selected from the group consisting of $^{13}C$; $^{15}N$; and $^{13}C$ and $^{15}N$. In one embodiment of the invention, the method comprises preparing RNA or DNA wherein each isotopically enriched chemical element comprised in RNA or DNA is isotopically enriched to between about 99.90 atom % and about 99.99 atom % purity. In another embodiment of the invention, the method comprises preparing RNA or DNA wherein each isotopically enriched chemical element comprised in RNA or DNA is isotopically enriched to between about 99.93 atom % and about 99.98 atom % purity. In yet another embodiment, the method described comprises preparing RNA, wherein the RNA is selected from the group consisting of mRNA, tmRNA, tRNA and rRNA.

Isotopically enriched nucleic acids may be harvested from microorganisms grown in accordance with the method of the present invention in any manner. Preferably the harvesting process results in such high purity DNA or RNA, for example, using techniques known to those of ordinary skill in the art including both organic and inorganic chemical extraction methods. In one aspect, the microorganism may be allowed to culture until a stationary phase is reached and isotopically enriched nucleic acids are harvested using one or more salting out methods.

Isotopically enriched DNA or RNA harvested from a microorganism or organism may be processed into nucleotides. Such a process generally includes the steps of hydrolyzing the DNA or RNA into nucleoside monophosphates, and phosphorylating the nucleoside monophosphates into nucleoside triphosphate. Each of the nucleoside triphosphates may then be separately isolated and purified. Typically, the deoxynucleoside triphosphates are recovered as triethylammonium salts. In another aspect, isotopically enriched DNA or RNA harvested from a microorganism may be processed into nucleosides and subsequently phosphorylated into nucleotides.

In one embodiment of the invention, the isotopically enriched nucleic acids, nucleoside monophosphates, and nucleoside triphosphates can be selectively labeled or selectively derivatized to increase their mass. Incorporation of such mass tags into nucleotides can increase the relative mass differences between specific nucleotides, thereby facilitating identification of DNA sequence or genetic change, such as, for example, SNPs, using mass spectrometry. Isotopic enrichment with $^{15}N$ in a nucleic acid isotopically enriched in one or more of the constituent chemical elemental isotopes selected from the group consisting of $^{12}C$; $^{16}O$; $^{16}O$ and $^{12}C$ results in an increased mass difference between A and T nucleotides to 3 Da. This additional 3 Da mass difference improves the ability to resolve an A/T heterozygote mass spectrometrically and therefore, increases the size of PCR products or nucleic acids that can be analyzed to distinguish an A/T difference.

In particular, the mass tag may also be a derivative of a nucleotide, nucleoside, or nucleic acid, in which the derivative moiety is isotopically enriched. Nucleotides or nucleic acids, which are isotopically enriched in one or more of the constituent chemical elemental isotopes selected from the group consisting of $^{12}C$; $^{16}O$; $^{16}O$ and $^{12}C$; and $^{14}N$, $^{16}O$, and $^{12}C$, can be derivatized at the nucleobase, sugar, or phosphate moieties. For example, the nucleobases adenine and guanine can be methylated with an isotopically enriched $^{12}CH_3$ group. Specific nucleotides can be derivatized; for example, methylation of only the A nucleotides results in an increased mass difference of 14 Da between A and T nucleotides, such that the net mass difference between A and T nucleotides is now 23 Da (rather than the normal difference of 9 Da). This additional mass difference greatly improves the ability to separate and distinguish A/T SNP heterozygote DNA molecules mass spectrometrically and, therefore, increases the size of PCR products or nucleic acids that can be analyzed. In one aspect, both A and guanosyl (G) nucleotides are methylated, such that the mass difference between A and G nucleotides remains at 16 Da, while A and T nucleotides differ by 23 Da. In this aspect, the minimum mass difference between any two nucleotides is 15 Da (e.g., for heterozygote SNPs, C/T is 15 Da, C/A is 38 Da, C/G is 54 Da, T/A is 23 Da, T/G is 39 Da, and A/G is 16 Da).

In one embodiment of the invention, nucleotides may be derivatized with one or more methyl groups, depending on the nucleotide and methylation chemistry. In another embodiment, nucleotides may be derivatized with one or more different functional groups, depending on the nucleotide and methylation chemistry. Various derivatives may be employed, including, but not limited to, various alkylations, amidations, and thiolations.

In one embodiment of the invention, the isotopically enriched nucleic acids or nucleotides further comprise a mass tag. In another embodiment, the method for providing a mass tag is selected from the group consisting of $^{15}N$ incorporation and $^{12}CH_3$ methylation. One embodiment of the invention is a DNA or RNA isotopically enriched in one or more of the constituent chemical elemental isotopes selected from the group consisting of $^{16}O$; $^{16}O$ and $^{12}C$; and $^{12}C$, $^{14}N$ and $^{16}O$, wherein the DNA or RNA comprises one or more nucleotides derivatized with one or more methyl groups, wherein said methyl groups are isotopically enriched with $^{12}C$. In another embodiment of the invention, the derivatized nucleotides, which are isotopically enriched in one or more of the constituent chemical elemental isotopes selected from the group consisting of $^{16}O$; $^{16}O$ and $^{12}C$; and $^{12}C$, $^{14}N$ and $^{16}O$, are selected from the group consisting of adenosine triphosphate, thymidine triphosphate, guanosine triphosphate and combinations thereof. These derivatized nucleotides can comprise ribose or deoxyribose. Another embodiment of the invention is nucleoside or nucleotide isotopically enriched in one or more of the constituent chemical elemental isotopes selected from the group consisting of $^{16}O$; $^{16}O$ and $^{12}C$: and $^{12}C$, $^{14}N$ and $^{16}O$, wherein the nucleoside or nucleotide is derivatized with one or more methyl groups, wherein said methyl groups are isotopically enriched with $^{12}C$.

One aspect of the invention provides a method for the preparation of a nucleoside monophosphate in which the nucleoside monophosphate is isotopically enriched in one of the isotopes of oxygen, the method comprising the steps of: (a) producing DNA or RNA in an organism grown in a growth medium in which the nutrients, reagents and solvents are isotopically enriched in one of the isotopes of oxygen; (b) isolating the isotopically enriched DNA or RNA; (c) hydrolyzing the isotopically enriched DNA or RNA water enriched in the same isotope oxygen. One embodiment of the invention provides a method for the preparation of a nucleoside monophosphate in which the nucleoside monophosphate is isotopically enriched in one or more of the constituent chemical elemental isotopes selected from the group consisting of $^{16}O$; $^{16}O$ and $^{12}C$; and $^{12}C$, $^{14}N$ and $^{16}O$, the method comprising the steps of: (a) producing DNA or RNA in an organism grown in a growth medium in which the nutrients, reagents and solvents are isotopically enriched in one or more of the constituent chemical elemental isotopes selected from the group consisting of $^{16}O$; and $^{12}C$, $^{14}N$ and $^{16}O$; (b) isolating the isotopically enriched DNA or RNA; (c) hydrolyzing the isotopically enriched DNA or RNA in $^{16}O$ enriched water. In one embodiment of the invention, the nucleoside monophosphate and the nutrients, reagents and solvents of the growth medium are isotopically enriched in $^{16}O$. In another embodiment, the nucleoside monophosphate and the nutrients, reagents and solvents of the growth medium are isotopically enriched in $^{12}C$, $^{14}N$ and $^{16}O$. In yet another embodiment, the nucleoside monophosphate and the nutrients, reagents and solvents of the growth medium are isotopically enriched in $^{16}O$ as well as in one or more constituent chemical elemental isotopes selected from the group consisting of $^{13}C$; $^{15}N$; and $^{13}C$ and $^{15}N$.

A wide variety of suitable endonucleases may be used for hydrolyzing extracted DNA or RNA, and the selection of specific endonucleases may be based in part on the particular DNA or RNA used. In one embodiment of the invention, in the method of preparing a nucleoside monophosphate or a nucleoside triphosphate, the hydrolysis is accomplished with P1 endonuclease. The amount of the selected endonuclease which is required to effect the desired hydrolysis of a specific amount of DNA or RNA may be determined by one of ordinary skill in the art without undue experimentation.

The hydrolysis reaction used in the present invention for the formation of nucleoside monophosphates may be carried out under a variety of conditions and includes a variety of steps that are specifically chosen to achieve a particular result. However, in one aspect of the invention, the hydrolysis reaction may be carried out by combining the DNA or RNA into an aqueous reaction mixture with P1 endonuclease and appropriate buffers and salts, and allowing the mixture to incubate for about 2 hours at a temperature of about 45° C. In one embodiment of the invention, $^{16}$O-enriched water is employed in the hydrolysis reaction. In general, the hydrolysis can be performed between 37° C. and 55° C., with addition of three aliquots of enzyme over the course of 18–24 hours, where the DNA is denatured prior to each round of hydrolysis.

To achieve a desired result and ensure maximum nucleoside monophosphate production, the above recited process may be repeated multiple times before performing the step of phosphorylating the nucleoside monophosphates into nucleoside triphosphates. Additionally, when DNA or RNA is being used (prior to adding the P1 enzyme), the DNA or RNA is first boiled, or otherwise treated, in order to denature it, followed by quenching in an ice bath. Additionally, a DNase enzyme may be added to DNA to partially hydrolyze the DNA into fragments prior to the addition of the P1 endonuclease. In one embodiment, RNase-free DNase is added to the DNA and incubated at 55° C. for one hour.

In one aspect of the invention, the nucleoside monophosphates may be further processed prior to the phosphorylation thereof into nucleoside triphosphates. In particular, impurities such as salts, proteins, and other contaminants may be removed using one or more suitable ion exchange and/or reverse-phase high performance liquid chromatography (HPLC) methods. A variety of such methods are known to those skilled in the art, and a particular method may be selected in order to achieve a specific result, such as the removal of particular impurities. Further, multiple chromatography methods may be combined in order to remove multiple impurities which may not be simultaneously removed using a single chromatography method. In one embodiment of the invention, the method of isolating and purifying a nucleoside monophosphate employs reverse-phase and/or anion-exchange chromatography. In yet another embodiment, the anion exchange chromatography employs columns containing chromatographic media selected from the group consisting of diethylamino (DEA), diethylaminoethyl (DEAE), amino, and strong anion exchange (SAX). In yet another embodiment, the method further comprises collecting a nucleoside monophosphate using at least one HPLC column selected from the group consisting of reverse phase analytical, reverse-phase semi-preparative and reverse-phase preparative columns.

In one detailed aspect of the invention, the purification of the nucleoside monophosphates may include the steps of passing the nucleoside monophosphates through a reverse-phase chromatography C18 column (100 mg, disposable solid-phase extraction column; Varian (Palo Alto, Calif.)) using a 5% acetonitrile mobile phase, collecting the nucleoside monophosphates, drying the nucleoside monophosphates, and azeotroping the nucleoside monophosphates with water. In another aspect, multiple azeotropings may be performed. Following azeotroping, the nucleoside monophosphates may be re-suspended in about 2 mL of water and eluted over a strong-anion exchange (SAX) column (100 mg, disposable solid-phase extraction column; Varian) that has been previously equilibrated with water. Nucleoside monophosphates may then be eluted with 0.6 M TEABC at pH 9.0, and evaporated, azeotroped, and re-suspended as recited above. Notably, HPLC-grade or water purified to approximately 18.3 megohm-cm ("18.3 megohm water") may be used throughout all isolations and purifications. Isotopically enriched water comprising $^{16}$O can be used to minimize the risk of introducing multiple oxygen isotopes.

In one embodiment of the invention, the method further comprises isolating an isotopically enriched nucleoside monophosphate selected from the group of adenosine monophosphate, guanosine monophosphate, thymidine monophosphate, and cytidine monophosphate. The nucleotides can comprise ribose or deoxyribose. In another embodiment of the invention, the method comprises preparing a nucleoside monophosphate wherein each isotopically enriched chemical element comprised in the nucleoside monophosphate is isotopically enriched to between about 99.90 atom % and about 99.99 atom % purity. In another embodiment, the method comprises preparing a nucleoside monophosphate wherein each isotopically enriched chemical element comprised in the nucleoside monophosphate is isotopically enriched to between about 99.93 atom % and about 99.98 atom % purity.

In yet another embodiment, the method comprises preparing a nucleoside monophosphate wherein the nucleoside monophosphate is dAMP. In yet another embodiment, the method comprises preparing a nucleoside monophosphate wherein the nucleoside monophosphate is dGMP. In yet another embodiment, the method comprises preparing a nucleoside monophosphate wherein the nucleoside monophosphate is dCMP. In yet another embodiment, the method comprises preparing a nucleoside monophosphate wherein the nucleoside monophosphate is dTMP.

In another embodiment, the isotopically enriched nucleoside monophosphate can be prepared using standard synthetic chemistry techniques in which the constituent chemical elemental isotopes selected from the group consisting of $^{16}$O; $^{16}$O and $^{12}$C; and $^{12}$C, $^{14}$N and $^{16}$O, comprised in the reactants are isotopically enriched. In yet another embodiment, the isotopically enriched nucleoside monophosphate can be prepared using standard synthetic chemistry techniques in which the reactants are isotopically enriched in $^{16}$O as well as in constituent chemical elemental isotopes selected from the group consisting of $^{15}$N; $^{13}$C; and $^{13}$C and $^{15}$N.

The step of phosphorylating the nucleoside monophosphates into nucleoside triphosphates may be accomplished using any suitable method known to those ordinarily skilled in the art. However, in one aspect of the present invention, the nucleoside triphosphates may be derivatized from nucleoside monophosphates using a reaction mixture that contains one or more phosphate donating molecules in combination with one or more nucleoside kinasing enzymes. Examples of specific phosphate-donating molecules which may be used include without limitation, ATP and phosphoenol pyruvate, as well as mixtures thereof. In one embodiment of the invention, the beta and gamma phosphate groups are not isotopically enriched. In another embodiment, the beta and gamma phosphate groups are isotopically enriched in $^{16}$O. In one embodiment of the invention, the nucleoside kinasing enzyme is selected from the group consisting of pyruvate kinase, guanylate kinase, nucleoside monophosphate kinase, myokinase, thymidylate kinase, and an $E.$ $coli$ kinasing enzyme fraction.

As recited above, the derivatizing reaction may be selected from a wide variety of reactions which would derivatize nucleoside monophosphates into nucleoside triphosphates. However, in one embodiment of the invention, the derivatization includes the step of incubating the nucleoside monophosphates in an aqueous mixture containing one or more of the above-recited phosphate donating molecules and one or more of the above-recited kinasing enzymes at about 37° C. for about 12 hours. In another aspect, the aqueous reaction mixture may include one or more buffer agents, such as Tris-HCl, magnesium chloride, potassium chloride, dithiothreitol (DTT), and mixtures thereof.

Another aspect of the invention is a method for the preparation of a nucleoside triphosphate in which the nucleoside triphosphate is isotopically enriched in one of the isotopes of oxygen, the method comprises the steps of: (a) producing DNA or RNA in an organism grown in a growth medium in which the nutrients, reagents and solvents are isotopically enriched in the same isotope of oxygen; (b) isolating the isotopically enriched DNA or RNA; (c) hydrolyzing the isotopically enriched DNA or RNA in water enriched in the same isotope of oxygen; (d) phosphorylating a nucleoside monophosphate using one or more nucleoside kinasing enzymes to produce a nucleoside triphosphate, wherein the nucleoside triphosphate comprises beta and gamma phosphate groups that are not isotopically enriched. Another aspect of the invention is a method for the preparation of a nucleoside triphosphate in which the nucleoside triphosphate is isotopically enriched in one or more of the constituent chemical elemental isotopes selected from the group consisting of $^{16}O$; $^{16}O$ and $^{12}C$; and $^{12}C$, $^{14}N$ and $^{16}O$, the method comprises the steps of: (a) producing DNA or RNA in an organism grown in a growth medium in which the nutrients, reagents and solvents are isotopically enriched in one or more of the constituent chemical elemental isotopes selected from the group consisting of $^{16}O$; $^{16}O$ and $^{12}C$; and $^{12}C$, $^{14}N$ and $^{16}O$; (b) isolating the isotopically enriched DNA or RNA; (c) hydrolyzing the isotopically enriched DNA or RNA in $^{16}O$ enriched water; (d) phosphorylating a nucleoside monophosphate using one or more nucleoside kinasing enzymes to produce a nucleoside triphosphate, wherein the nucleoside triphosphate comprises beta and gamma phosphate groups that are not isotopically enriched. In one embodiment of the invention, the nucleoside triphosphate and the nutrients, reagents and solvents of the growth medium are isotopically enriched in $^{16}O$. In another embodiment, the nucleoside triphosphate and the nutrients, reagents and solvents of the growth medium are isotopically enriched in $^{12}C$, $^{14}N$ and $^{16}O$. In yet another embodiment, the nucleoside triphosphate and the nutrients, reagents and solvents of the growth medium are isotopically enriched in $^{16}O$, as well as in one or more constituent chemical elemental isotopes selected from the group consisting of $^{13}C$; $^{15}N$; and $^{13}C$ and $^{15}N$.

In one embodiment of the invention, the method further comprises isolating an isotopically enriched nucleoside triphosphate selected from the group of adenosine triphosphate, guanosine triphosphate, thymidine triphosphate, and cytidine triphosphate. The nucleotides can comprise ribose or deoxyribose. In another embodiment of the invention, the method comprises preparing a nucleoside triphosphate wherein each isotopically enriched chemical element comprised in the nucleoside triphosphate is isotopically enriched to between about 99.90 atom % and about 99.99 atom % purity. In another embodiment of the invention, the method comprises preparing a nucleoside triphosphate wherein each isotopically enriched chemical element comprised in the nucleoside triphosphate is isotopically enriched to between about 99.93 atom % and about 99.98 atom % purity.

In yet another embodiment, the method comprises preparing a nucleoside triphosphate wherein the nucleoside triphosphate is dATP. In yet another embodiment, the method comprises preparing a nucleoside triphosphate wherein the nucleoside triphosphate is dGTP. In yet another embodiment, the method comprises preparing a nucleoside triphosphate wherein the nucleoside triphosphate is dCTP. In yet another embodiment, the method comprises preparing a nucleoside triphosphate wherein the nucleoside triphosphate is dTTP.

Following the formation of nucleoside triphosphates, like nucleoside triphosphates may be separated from the reaction mixture using HPLC. In one embodiment of the invention, the method of preparing a nucleoside triphosphate further comprises collecting the nucleoside triphosphate using at least one HPLC column selected from the group consisting of reverse phase analytical, reverse-phase semi-preparative and reverse-phase preparative columns. In yet another embodiment, the anion exchange chromatography employs columns containing chromatographic media selected from the group consisting of diethylamino (DEA), diethylaminoethyl (DEAE), amino and strong anion exchange (SAX).

The HPLC mobile phase buffer and volatile components may then be separated away from the nucleoside triphosphates by evaporation and azeotroping as set forth herein. The resultant isotopically enriched nucleoside triphosphates may then be stored dry or re-suspended in water for use in making second generation products.

In one embodiment of the invention, a method comprises preparing an isotopically enriched compound selected from the group consisting of nucleoside monophosphate, nucleoside triphosphate, RNA and DNA, wherein each isotopically enriched chemical element comprised in the isotopically enriched compound is isotopically enriched to at least 99.9 atom % purity. In another embodiment, each isotopically enriched chemical element comprised in the isotopically enriched nucleotide or oligonucleotide is isotopically enriched to at least about 99.93 atom % purity. In yet another embodiment, each isotopically enriched chemical element comprised in the isotopically enriched nucleotide or oligonucleotide is isotopically enriched to at least about 99.95 atom % purity. In yet another embodiment, each isotopically enriched chemical element comprised in the isotopically enriched nucleotide or oligonucleotide is isotopically enriched to at least about 99.99 atom % purity.

One aspect of the invention is a method of synthesizing DNA isotopically enriched in an isotope of oxygen. Another aspect of the invention is a method of synthesizing an isotopically enriched DNA comprising using a technique selected from the group consisting of polymerase chain reaction (PCR) amplification, reverse-transcriptase polymerase chain reaction (RT-PCR) amplification, oligo ligation amplification (OLA), rolling-circle amplification, and single nucleotide primer extension reaction (SNuPE), wherein the nucleoside triphosphate reagents are isotopically enriched in one or more of the constituent chemical elemental isotopes selected from the group consisting of $^{16}O$; $^{16}O$ and $^{12}C$; and $^{12}C$, $^{14}N$ and $^{16}O$, wherein the nucleoside triphosphate comprises beta and gamma phosphate groups that are not isotopically enriched. In one embodiment of the invention, the technique is selected from the group consisting of polymerase chain reaction (PCR) amplification and reverse-transcriptase polymerase chain reaction (RT-PCR) amplification. In another embodiment, the technique is polymerase chain reaction (PCR) amplification. The isotopically enriched second generation products can then be analyzed using mass spectrometry.

Another aspect of the invention is a method for determining the mass of an oligonucleotide, wherein the oligonucleotide is isotopically enriched in one of the isotopes of oxygen; the method comprises the steps of: (a) making an oligonucleotide isotopically enriched in the same isotope of oxygen; (b) determining the mass of the isotopically enriched oligonucleotide using mass spectrometry. Another aspect of the invention is a method for determining the mass of an oligonucleotide, wherein the oligonucleotide is isotopically enriched in one or more of the constituent chemical elemental isotopes selected from the group consisting of $^{16}O$; $^{16}O$ and $^{12}C$; and $^{12}C$, $^{14}N$ and $^{16}O$; the method comprises the steps of: (a) making an oligonucleotide isotopically enriched in one or more of the constituent chemical elemental isotopes selected from the group consisting of $^{16}O$; $^{16}O$ and $^{12}C$; and $^{12}C$, $^{14}N$ and $^{16}O$; (b) determining the mass of the isotopically enriched oligonucleotide using mass spectrometry. In one embodiment of the invention, the method further comprises the steps of: (a) producing DNA or RNA in organisms grown in a growth medium in which the nutrients, reagents and solvents are isotopically enriched in one or more of the constituent chemical elemental isotopes selected from the group consisting $^{16}O$; $^{16}O$ and $^{12}C$; and $^{12}C$, $^{14}N$ and $^{16}O$; (b) hydrolyzing the isotopically enriched DNA in $^{16}O$-enriched water; (c) phosphorylating the isotopically enriched nucleoside monophosphates; (d) using the resulting nucleoside triphosphate in a polymerase chain reaction amplification to prepare a DNA oligonucleotide isotopically enriched in one or more of the constituent chemical elemental isotopes selected from the group consisting of $^{16}O$; $^{16}O$ and $^{12}C$; and $^{12}C$, $^{14}N$ and $^{16}O$. In one embodiment, the oligonucleotide is isotopically enriched in $^{16}O$. In another embodiment, the oligonucleotide is isotopically enriched in the constituent chemical elemental isotopes $^{12}C$, $^{14}N$ and $^{16}O$. In yet another embodiment, the oligonucleotide is enriched in $^{16}O$ as well as one or more constituent chemical elemental isotopes selected from the group consisting of $^{13}C$; $^{15}N$; and $^{13}C$ and $^{15}N$. In another embodiment the oligonucleotide contains at least one known genetic variant selected from the group consisting of single nucleotide polymorphisms, deletions, insertions, and short-tandem repeat regions. In yet another embodiment, the oligonucleotide contains at least one unknown genetic variant selected from the group consisting of single nucleotide polymorphisms, deletions, insertions, and short-tandem repeat regions.

In one embodiment of the invention the method comprises determining the mass of an oligonucleotide comprising between about 50 nucleotides and about 2000 nucleotides. In another embodiment, the oligonucleotide comprises between about 150 nucleotides and about 1000 nucleotides. In another embodiment, the oligonucleotide comprises between about 100 nucleotides and about 600 nucleotides. In yet another embodiment, the oligonucleotide comprises between about 50 nucleotides and about 600 nucleotides. In yet another embodiment, the oligonucleotide comprises between about 80 nucleotides and about 500 nucleotides. In another embodiment, the oligonucleotide comprises between about 80 nucleotides and about 300 nucleotides. In another embodiment, the oligonucleotide comprises between about 80 nucleotides and about 200 nucleotides. In another embodiment, the method further comprises using the mass spectrometer in conjunction with electrospray ionization. In another embodiment, the method further comprises using the mass spectrometer in conjunction with matrix assisted laser desorption ionization.

Another aspect of the invention is a method of identifying a known or an unknown nucleic acid structural modification or genetic variant in an oligonucleotide, wherein the oligonucleotide is isotopically enriched in one isotope of oxygen, the method comprises the steps of: (a) making an oligonucleotide isotopically enriched in one isotope of oxygen; (b) determining the mass of the isotopically enriched oligonucleotide using mass spectrometry; wherein the genetic variant is selected from the group of single nucleotide polymorphisms, deletions, insertions, and short tandem repeat regions. Another aspect of the invention is a method of identifying a known or an unknown nucleic acid structural modification or genetic variant in an oligonucleotide, wherein the oligonucleotide is isotopically enriched in $^{16}O$, the method comprises the steps of: (a) making an oligonucleotide isotopically enriched in $^{16}O$; (b) determining the mass of the isotopically enriched oligonucleotide using mass spectrometry; wherein the genetic variant is selected from the group of single nucleotide polymorphisms, deletions, insertions, and short-tandem repeat regions.

Another aspect of the invention is method of identifying a known or an unknown nucleic acid structural modification or genetic variant in an oligonucleotide, wherein the oligonucleotide is isotopically enriched in $^{12}C$, $^{14}N$ and $^{16}O$, the method comprising the steps of: (a) making an oligonucleotide isotopically enriched in $^{12}C$, $^{14}N$ and $^{16}O$; (b) determining the mass of the isotopically enriched oligonucleotide using mass spectrometry; wherein the genetic variant is selected from the group of single nucleotide polymorphisms, deletions, insertions, and short-tandem repeat regions.

The Examples provided below are merely illustrative of various specific embodiments for the production and purification of isotopically enriched nucleic acids in accordance with the general methods and products disclosed herein and no limitation is intended thereby.

EXAMPLES

Ex. 1

Production of Isotopically Enriched Nucleic Acids

Isotopically enriched nucleic acids for analysis with mass spectrometry were produced according to the following procedure. All labware used was rinsed with water purified to approximately 18.3 megohm-cm ("18.3 megohm water") and dried for 15 minutes in an 80° C. oven. Reagents comprised of $^{12}C$, $^{16}O$, and/or $^{14}N$ in isotopically enriched form and all apparatii were placed in a glove box and the atmosphere was purged with argon (99.9% purity). Media were prepared in the argon atmosphere with the isotopically enriched reagents recited above and other high purity (>99.95%) reagents as follows:

3.8 mM ammonium sulfate ($^{16}O$ and $^{14}N$>99.95 atom % purity) (Isotec)
  29.8 mM potassium chloride (Fluka)
  30 mM potassium phosphate ($^{16}O$>99.95 atom % purity) (Isotec)
  0.5 mM magnesium chloride (E M Scientific)
  5.6 mM glucose ($^{16}O$ and $^{12}C$>99.95 atom %) (Isotec)
  0.06 mM calcium chloride (E M Scientific)
  4.3 mM sodium chloride (J T Baker)

The final volume was brought up with isotopically enriched water comprising $^{16}O$ ($^{16}O$>99.95 atom % purity) (Isotec).

E. coli was then grown using the isotopically enriched media as follows. Five milliliters of the media were placed into a 15 mL conical polypropylene centrifuge tube and 2 μL of an E. coli glycerol stock (grown under rich media and natural isotope reagents and conditions) were added in the presence of room air to allow for displacement of the argon atmosphere in the tube. The sample was incubated (without aeration) at 37° C. with constant shaking for 25 hours. The 5 mL overnight culture was added to an aerated flask (i.e. rinsed and dried as previously described) containing 95 mL of isotopically enriched minimal media. All transfers were made in an argon atmosphere. The flask was capped with a rubber stopper with attached tubing that allowed the flask to be continuously purged with $^{16}$O-enriched oxygen (16O) >99.98 atom % purity) during incubation. The culture was incubated at 37° C. on an orbital shaker (300 rpms) for approximately 17 hours or until the cells reached the stationary phase of cell growth.

Ex. 2

Purification of Nucleic Acids

Isotopically enriched DNA was harvested from the E. coli cell culture grown above according to the following procedure. All steps of the DNA isolation were performed in standard room atmosphere. After incubation, 25 mL aliquots of the cell culture were transferred to an appropriate number of 50 mL conical polypropylene centrifuge tubes and centrifuged at 1000× g for 10 minutes to pellet the cells. The supernatant was decanted from the pellet. To each tube 15 mL of cell-lysis solution (PureGene reagent; Gentra Systems, Minneapolis, Minn.) were added and the solution was gently pipetted up and down until the cells were re-suspended. Samples were incubated at 80° C. for 5 minutes to lyse the cell membranes. If after 5 minutes the cells did not appear to be completely lysed, then the cell suspension was incubated for an additional 5 minutes or until lysis appeared complete (i.e. no cellular aggregate or clumps present).

To each cell lysate 75 μL RNAse A Solution (PureGene reagent; Gentra Systems) were added and mixed by inversion. The samples were incubated for 60 minutes at 37° C., and then cooled to room temperature, whereupon 5 mL of protein precipitation solution (PureGene reagent; Gentra Systems) were added and vortexed vigorously for 30 seconds. The samples were placed on ice for 5 minutes and then centrifuged at 2000× g for 10 minutes.

The supernatant, which contained the DNA, was decanted into a new 50 mL polypropylene centrifuge tube that contained 15 mL 100% isopropanol. The sample was gently mixed by inversion (50 times) to precipitate the DNA and then centrifuged at 2000× g for 10 minutes. The supernatant was decanted and discarded leaving a visible DNA pellet. The pellet was washed with 15 mL 70% ethanol then centrifuged at 2000× g for 5 minutes and the supernatant was decanted and discarded. The pellet was allowed to air dry for 15 minutes, re-suspended in an appropriate amount of $^{16}$O-water (>99.95 atom % purity), allowed to re-dissolve at room temperature, and then stored in a vacuum desiccator at 4° C.

Nucleotides for use in formulating second generation products for analysis with mass spectrometry were then produced from the extracted DNA as follows. The water used in all reagents was $^{16}$O-water (>99.95 atom % purity) to prevent exchanges with $^{17}$O and $^{18}$O isotopes present in natural isotopic abundance water and the atmosphere.

In an argon atmosphere, 125 μg of DNA was digested with P1 endonuclease in a final volume of 1 mL, as follows:

210 μL isotopically enriched DNA (125 μg at 596 μg/mL)
772 μL $^{16}$O water (>99.95 atom %)

The DNA mixture was removed from the argon atmosphere and boiled (approximately 100° C.) in a dry bath for approximately 8 minutes to denature the DNA tertiary structure, followed by quenching in an ice bath for 8 minutes. To the denatured DNA solution, 50 mM sodium acetate (pH 5.3) and 0.1 mM zinc sulfate were added and mixed. P1 endonuclease was added to the mixture in the amount of 1.5 units, and mixed gently. The mixture was then incubated at 46° C. for 2 hours. After incubation, the DNA was again denatured and quenched as recited above, and an additional 1.5 units of P1 endonuclease was added and incubation continued at 46° C. for 2 hours. Finally, the DNA was again denatured, quenched, and another 1.5 units of P1 added and allowed to incubate again at 46° C. for approximately 8–12 hours.

After incubation, 50 μL 100% acetonitrile were added to the sample. The sample was then purified over a reverse-phase C18 column followed by a strong-anion exchange column as follows:

A C18 reverse-phase column (100 mg, disposable solid-phase extraction column, Vydac (Hesperia, Calif.)) was prepared as follows (flow rate no more than 1 mL/minute):

1. 2×1 mL 100% acetonitrile
2. 3×1 mL 5% acetonitrile (v/v)
3. load sample (1 mL with 5% acetonitrile (v/v) as previously reconstituted) and collect flow-through
4. 1×500 μL 5% acetonitrile (v/v) and collect flow-through The collected flow-through was then evaporated until dry and azeotroped with 75 μL 18.3 megohm water followed by evaporation of the liquid until dry. The nucleoside monophosphates were then resuspended in 2 mL 18.3 megohm water and further purified by desalting with a strong-anion exchange (SAX) column (100 mg, disposable solid-phase extraction column, Varian) as follows:

1. 2×1 mL methanol
2. 2×1 mL 18.3 megohm water
3. 2×1 mL 1 M ammonium acetate
4. 4×1 mL 18.3 megohm water
5. load sample onto column (2×1 mL water)
6. 2×1 mL water
7. 1×1 mL 0.6 M triethylammonium bicarbonate (TEABC) pH 8–9 and collect flow-through As above, the collected flow-through was evaporated until dry then azeotroped two times with 75 μL water and evaporated to dryness. The nucleoside monophosphates were then resuspended in 60 μL $^{16}$O-water (>99.95 atom %).

Nucleoside triphosphates were then produced using the processed nucleoside monophosphates according to the following procedure. Once again $^{16}$O-water (>99.95 atom %) may be used in all reactions and solutions during the phosphorylation procedure to prevent or reduce possible exchanges of $^{16}$O isotopic with $^{17}$O and $^{18}$O isotopes, from exposure to natural water which would contain natural isotopic levels of $^{17}$O and $^{18}$O isotopes.

To the 60 μL of purified dNMPs, the following solution of reagents was added in a total volume of approximately 100 μL to phosphorylate the dNMPs to dNTPs:

75 mM phospho-enol pyruvate
80 mM Tris-HCl pH 7.6
20 mM potassium chloride
20 mM magnesium chloride
10 mM dithiothreitol
1 nanomole ATP
0.8 units pyruvate kinase
0.002 units guanylate kinase 0.01 units nucleoside monophosphate kinase
0.2 units myokinse
0.5–5 μL thymidylate kinase (component of an *E. coli* kinasing enzyme fraction)

The phosphorylation reaction mixture was incubated at 37° C. for approximately 12 hours. After incubation, 50 μL 100% acetonitrile and 850 μL of water were added and mixed. The dNTPs were then subjected to the same C18/SAX column purification as outlined above for the dNMPs. After the final evaporation step, the dNTPs were re-suspended in 200 μL of 26 mM TEABC buffer (pH 8.3) with 2.25% acetonitrile (v/v).

The individual nucleotides were collected using an analytical C18 reverse-phase HPLC column (ZORBAX C18 column, Agilent Technologies (Wilmington, Del.)) equilibrated with 26 mM TEABC (pH 8.3) with 2.25% acetonitrile (v/v) at a flow rate of 0.75 mL/minute (isocratic conditions). A reverse-phase semi-preparative or reverse-phase preparative column could also be used depending on the amount of nucleotides being collected. The chromatographic results of the separation are shown in FIG. 1. FIG. 1 is an HPLC chromatogram following reverse-phase and anion-exchange purification steps after phosphorylation. Highlighted peaks (in grey) are the triphosphorylated deoxynucleotides (dNTP's) in which the nucleoside and alpha phosphate moieties are isotopically enriched to greater than 99.90 atom % in 12C, $^{16}$O, and $^{14}$N. The highlighted areas indicate fractions collected for each dNTP produced.

Figure 2:
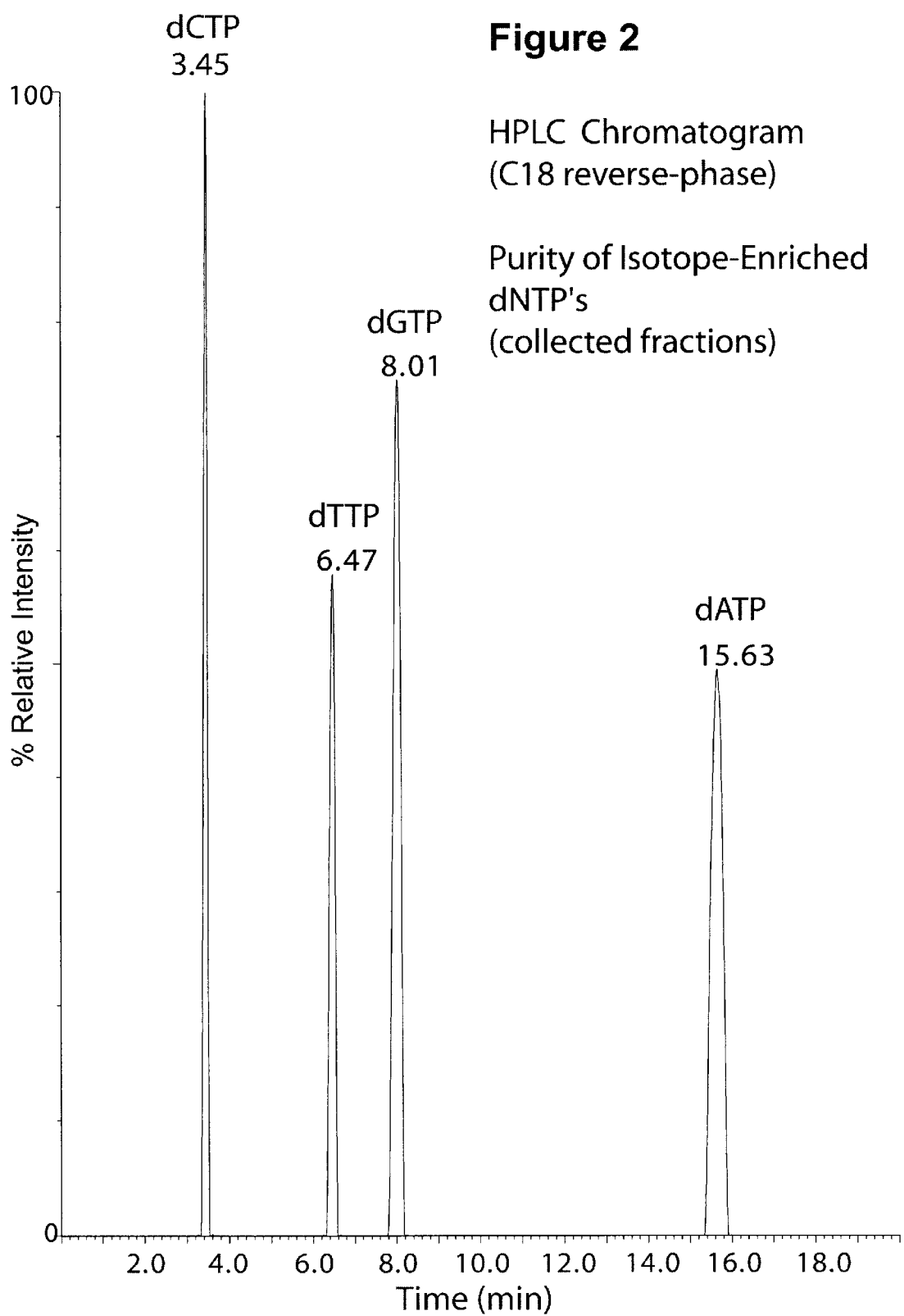
FIG. 2 is an HPLC chromatogram showing the purity of the isotopically enriched dNTP fractions collected (refer to FIG. 1), as described in Example 2.

The purified nucleotides in a volume of 200 μL were further injected in 50 μL aliquots over the ZORIBAX C18 column (analytical HPLC C18 reverse-phase column). Peaks corresponding to the individual dNTPs were collected as a further step for purification and isolation from contaminates and minor levels of mono- and diphosphate deoxyribonucleosides. After collection, the dNTPs were evaporated to dryness and azeotroped two times with 75 μL water. FIG 2 indicates the purity of the collected fractions (from FIG 1). The dNTPs were either stored dry or re-suspended in water or $^{16}$O-water (>99.95 atom %), as ready to use for PCR reactions or other applications.

Ex. 3

Formation of Second Generation Products

General Parameters and Conditions

The PCR reaction set-up is described below and typical conditions are listed in Table 1. The reactions are assembled in a clean, dust-free environment. All vials and plastics used are rinsed with 18.3 megohm water to remove particulates, contaminants, and traces of plasticizers that could inhibit PCR reactions, sample cleanup and subsequent analysis with mass spectrometry. Generally, the PCR template (human genomic DNA) to be amplified is aliquoted into the PCR tray and placed on ice. The remainder of the PCR components are assembled as a master mix and then a portion of this mix is aliquoted into each vial with DNA template.

The DNA polymerase used is Diamond DNA polymerase, (Bioline USA, Inc., Randolph, Mass.) which has been selected due to its high fidelity and low propensity to generate non-templated artifacts. Spermidine is added to the PCR reaction mixture and to enhance amplification, by increasing interaction of the primer with the genomic DNA template.

TABLE 1

PCR reaction mixture. Total Volume of 100 μL with 5 μL of template representing 25–100 ng of human genomic DNA. The amount of dNTPs used in the PCR reaction is determined by the length of the expected PCR products.

| PCR Master Mix | 1X Amount |
|---|---|
| 10X NH$_4$SO$_4$ Buffer | 10 μL |
| dNTPs (1.0 mM) | 10–30 μL |
| Forward primer (25 μM) | 2–4 μL |
| Reverse primer (25 μM) | 2–4 μL |
| Spermidine-HCl (50 mM) | 0.5 μL |
| Bioline Diamond polymerase (5 μg/μL) | 0.5–1 μL |
| Water | q.s. to 95 μL |

The cycling conditions are performed using an Applied Biosystems 9700 thermocycler as follows:

| 1 cycle | |
|---|---|
| 94° C. | 5 minutes |
| 5 cycles | |
| 94° C. | 10 seconds |
| 58–60° C. | 10 seconds (determined by primer melting temp., Tm) |
| 72° C. | 20 seconds |
| 30 cycles | |
| 94° C. | 10 seconds |
| 53–55° C. | 10 seconds (annealing temperature less 5° C.) |
| 72° C. | 20 seconds |

Samples are immediately removed from the PCR machine upon completion of the cycling and quick chilled in an ice bath or freezer, to minimize formation of non-template polymerization artifacts.

Ex. 4

PCR Product Purification

DNA from the PCR reaction above is purified and suitably prepared for analysis by mass spectrometry using an ammonium acetate ion-exchange and ethanol precipitation. This procedure serves to desalt the DNA and remove proteins and other contaminants. The protocol effectively removes trace levels of sodium and potassium salts to afford efficient ionization and successful analysis of large DNA molecules by ESI/MS or MALDI/MS, such that salt-adduct ions are greatly reduced or eliminated.

The process for purification of PCR products is as follows.

a) Prepare a polypropylene microcentrifuge tube (or 96-well or 384-well plates) to be used for precipitating a DNA sample by scoring the bottom/side of the polypropylene microcentrifuge tubes with a sharp metal point in such a location to provide a small roughened surface (scratch mark) for the DNA pellet to adhere to during centrifugation. (This permits more rigorous handling and prevents losses of DNA pellets. DNA pellets can be inadvertently lost from the normally smooth surface of polypropylene tubes during decanting steps especially the ethanol wash step, see below.) Tubes are then rinsed with 18.3 megohm water to remove any plasticizers and/or surface contaminants.

b) Transfer the entire contents of a PCR reaction (approx. 100 μL aqueous solution) into the microcentrifuge tube.

(For difference PCR reaction volumes, steps described below can be adjusted to maintain proportional concentrations).

c) Add 50 µL of 8.5 to 9.0 M ammonium acetate (99.99% minimum purity; in 18.3 megohm water) and mix gently to a homogeneous solution, allowing ion exchange to take place for a few minutes at room temperature.

d) Add 450 µL of absolute ethanol (e.g. Aldrich, cat # E702-3) at room temperature, then mix gently to a homogeneous solution.

e) Allow the precipitation to take place for 15 to 24 hrs at −20° C.

f) Centrifuge at 15000 RPM (21000 RCF) for 60 minutes.

g) Pour off the supernatant and carefully remove any residual liquid by aspiration. A pipet tip fitted to a tube with a small vacuum (approximately 5 mm Hg) can be used to aspirate and remove trace liquid, being careful not to inadvertently discard the DNA pellet.

h) Add 300 µL of 75% ethanol. Gently mix without inverting.

i) Centrifuge at 15000 RPM (21000 RCF) for 15 minutes.

j) Pour off the supernatant and gently remove the residual liquid as described above. Vacuum dry the pellet for 10 to 30 secs. The DNA pellet will appear translucent.

The purified PCR products can now be analyzed by ESI/MS or MALDI/MS or can be stored dry.

Ex. 5

Sample Preparation for ESI MS a) Reconstitute the purified PCR product (described above) in 6–10 µL of a solution for electrospray ionization. This aqueous electrospray solution is comprised of about 45% acetonitrile (HPLC-grade) (v/v), about 51% water (18.3 megohm), and 3–4% triethylamine (spectroscopic grade, Sigma) (v/v). The purified DNA pellet will readily dissolve into solution.

b) Draw the DNA sample into a syringe or disposable tip as follows:

5–10 µL aliquot of solvent (i.e. solution in part (a))

5 µL aliquot of air

1–10 µL aliquot of sample in electrospray solution (i.e. solution in part (a) above)

c) Introduce the sample into the ESI probe of the mass spectrometer at a flow rate of 3–4 µL /min by infusion using a syringe pump.

Ex. 6

Analysis of Second Generation Products

DNA is analyzed by ESI/MS, performed with either a quadrupole or time-of-flight (TOF) mass spectrometer (e.g. Quattro II or LCT, Micromass, Inc.), although other instrument designs (e.g. FTICR) can be used with electrospray ionization.

a) MS preparation

The ESI probe assembly, tubing, and sample-introduction apparatus are sufficiently cleaned (i.e. salts, proteins, and other contaminants are removed at or below trace level) to minimize ionization suppression effects, salt adduction, or eliminate interference therefrom. Minimal capillary tubing length and apparatus for sample introduction are used (e.g. minimize surface area in contact with the sample, and therefore reduce potential for interfering contaminants). Specifically, polyetheretherketone (PEEK) tubing with 0.025" inch diameter is used.

Electrospray probe, tubing, sample-introduction apparatus, and syringe are prepared as follows:

1) rinse with 5 to 10% formic acid (about 150 to 200 µL) (v/v)

2) rinse with 18.3 megohm water (about 300 to 500 µL)

3) rinse with HPLC-grade methanol (100 to 200 µL)

4) rinse with 18.3 megohm water (about 300 to 500 µL)

5) clean the syringe as in steps 1–4 (clean the plunger and barrel individually)

b) Instrument parameters and ESI conditions

Spectra are acquired in the negative-ion mode and data collected in the mass/charge (m/z) range from approximately 650 to 1500 Da at 2 to 5 seconds per scan. Individual scans are accumulated for 15 seconds to 1 minute. The ESI probe voltage is generally optimized for ionization of large DNA molecules at 2.5 to 3 kV, but is dependent on the specific ESI probe design and set up. The ESI source is set at low ion-extraction cone voltage to ionize and accelerate large DNA ions with minimal collision dissociation.

An ESI cone voltage of about 30 eV is used. The ESI ion source temperature is maintained at about 75° C. The desolvation and nebulization gas ($N_2$) is optimized for flow rate and pressure in the spray atmosphere for highest ionization efficiency. Higher pressure ESI conditions may assist ionization of large DNA.

Data can be acquired using Masslynx software (Micromass, Inc.) and multiply-charge ion series can be deconvoluted and processed into neutral "molecular mass spectra" using Biolyxn and MaxEnt software (Micromass, Inc.).

Mass spectra for FIGS. 3–6 were acquired under identical conditions using negative-ion electrospray on a time-of-flight mass spectrometer (LCT, Micromass, Inc.). Data were collected in the mass range (m/z) of 700–1200 Da at 3 seconds data accumulations (20,000 Hz pusher frequency; 50 ns data accumulation per pulse), and scans were accumulated for a total acquisition time of 1 minute. The mass spectrometer was set to a resolution of 5000. The signal was sampled with a 4 GHz TDC (time/digital converter). The electrospray probe voltage was set to 2500 V and the sample cone was at 35 eV. The electrospray ion source and desolvation lens temperatures were maintained at 75° C. and 125° C., respectively. Nitrogen was used as electrospray nebulization gas at a flow rate of about 40 L/hr. Nitrogen was also used for desolvation gas at a flow rate of 170 L/hr. PCR samples were introduced by infusion into the mass spectrometer after reconstituting the DNA sample in an 8 µL solution of 50% water, 46.5% acetonitrile and 3.5% triethylamine (v/v) at a flow rate of 3.5 µL/minute. The multiply-charged molecular-ion series obtained in the analog mass spectra were deconvoluted and processed into "molecular mass spectra" using Biolynx and MaxEnt software (Micromass, Inc.), in which peak width parameters were established according to the actual average analog peak widths of molecular ions obtained for either natural-isotope PCR products (for example, 0.5 Da peak width at half height) or isotope-enriched PCR products (for example, 0.2 Da peak width at half height).

All other sample and mass spectrometer preparations were as outlined in the specifications.

Figure 3:
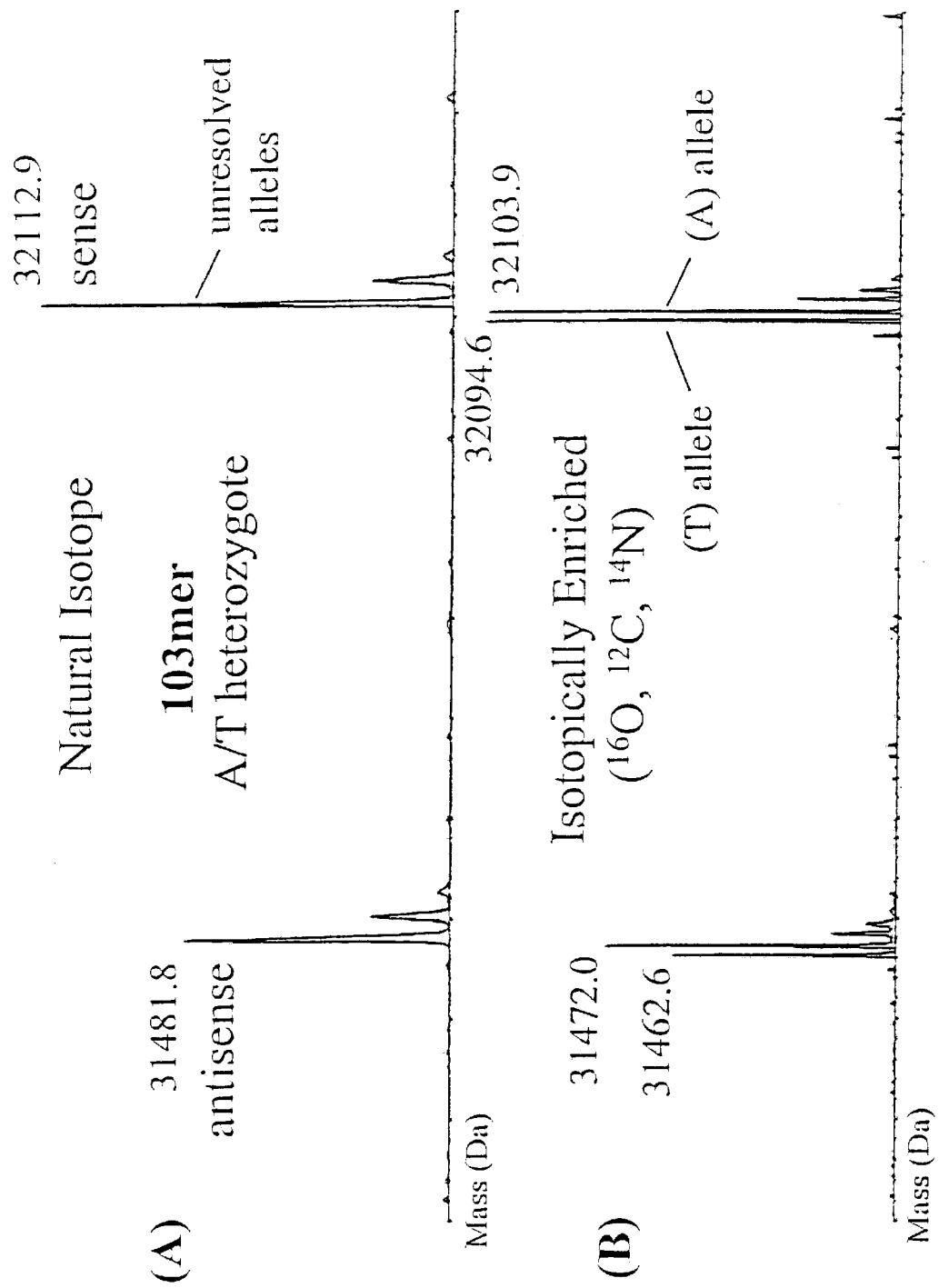
FIG. 3A shows the molecular mass spectrum of PCR products generated using natural-isotope dNTP's of a 103 nucleotide product of a region of the *adenomis polyposis coli* (APC) gene, in which a known A/T (adenosyl/thymidyl) single nucleotide polymorphism (SNP) occurs at gene sequence position 3920.
FIG. 3B is the molecular mass spectrum of isotopically enriched PCR products of the same sequence shown in FIG. 3A.

FIG. 3 is a comparison of mass spectra showing the analysis of DNA products generated from PCR amplification of a region of the *adenomis polyposis coli* (APC) gene, in which a known A/T single nucleotide polymorphism (SNP) occurs at gene-sequence position 3920. The DNA sample analyzed is heterozygous (A/T) at the 3920 position. Genomic DNA was used for PCR template. The PCR products analyzed are 103 nucleotides in length (103 mer). FIG. 3A shows the molecular mass spectrum of PCR products generated using natural-isotope dNTP's; FIG. 3B is the molecular mass spectrum of isotopically enriched PCR products in which each DNA molecule is isotopically enriched to greater than 99.90 atom % in $^{12}C$, $^{16}O$ and $^{14}N$. Both sense and antisense DNA strands are shown in FIG. 3A and 3B. The molecular weight of A/T SNP heterozygous alleles differ in mass by 9 Da. Note that the measured mass or molecular weight of the natural-isotope PCR products is higher than the corresponding isotopically enriched molecules, as a result of the total isotope composition in each product. The primer portion of the sense strand was removed by hydrolysis with a restriction enzyme prior to analysis. As shown, using conventional nucleotides the A/T heterozygous alleles are mass spectrometrically unresolved (FIG. 3A). By contrast, significant resolution is achieved for the A and T alleles in the isotopically enriched PCR products, for both the sense and anti-sense strands (FIG. 3B). Such improved resolution and sensitivity represents an advancement for analyzing and identifying genetic variants by mass spectrometry.

A molecular mass spectrum is a processed spectrum that represents the neutral molecular weight for each DNA molecule in the corresponding analog mass spectrum. A molecular mass spectrum is generated by deconvolution of the multiply-charged molecular-ion series produced by electrospray ionization.

Figure 4:
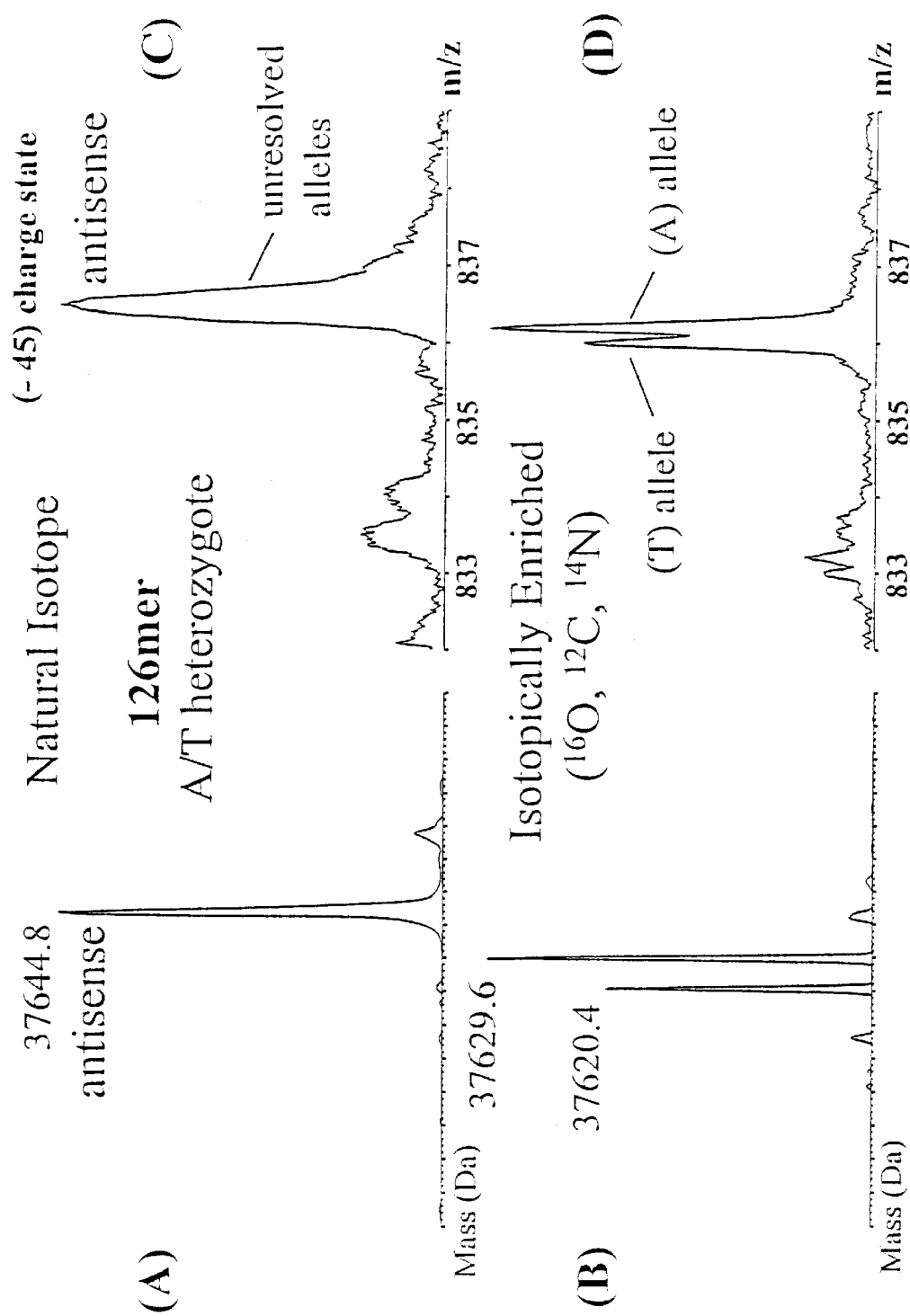
FIG. 4A shows the molecular mass spectrum of PCR products generated using natural-isotope dNTP's of a 126 nucleotide product of a region of the *adenomis polyposis coli* (APC) gene, in which a known A/T SNP occurs at gene sequence position 3920.
FIG. 4B is the molecular mass spectrum of isotopically enriched PCR products of the same sequence shown in FIG. 4A.
FIGS. 4C and 4D show a small region of the analog mass spectrum corresponding to the processed molecular mass spectra in FIGS. 4A and 4B, respectively.

FIG. 4 is a comparison of mass spectra showing the analysis of DNA products generated from PCR amplification of a region of the *adenomis polyposis coli* (APC) gene, in which a known A/T single nucleotide polymorphism (SNP) occurs at gene-sequence position 3920. The DNA sample analyzed is heterozygous (A/T) at the 3920 position. Genomic DNA was used for PCR template. The PCR products analyzed are 126 nucleotides in length (126 mer). FIG. 4A shows the molecular mass spectrum of PCR products generated using natural-isotope dNTP's; FIG. 4B is the molecular mass spectrum of isotopically enriched PCR products in which each DNA molecule is isotopically enriched to greater than 99.90 atom % in $^{12}C$, $^{16}O$ and $^{14}N$. PCR products for the antisense DNA strands are shown in FIG. 4 (sense strands are not shown in the figure). FIGS. 4C and 4D show a small region of the analog mass spectrum corresponding to the processed molecular mass spectra in FIGS. 4A and 4B, respectively. The alleles (A/T heterozygote) for each strand are mass spectrometrically unresolved for PCR products produced with natural isotopes (FIGS. 4A, 4C). By comparison, the alleles (A/T heterozygote) are separated and well resolved for isotopically enriched PCR products (FIGS. 4B, 4D). This benefit is supported in both the multiply-charged analog mass spectrum as well as the processed molecular mass spectrum, in which peak widths for each allele are narrower and mass spectrometrically separated. By comparison, the peaks for PCR products containing natural-isotope abundances indicate no mass spectrometric separation or distinction of the A/T heterozygosity. Note that the measured mass or molecular weight of the natural-isotope PCR products is higher than the corresponding isotopically enriched molecules, as a result of isotope compositions.

Figure 5:
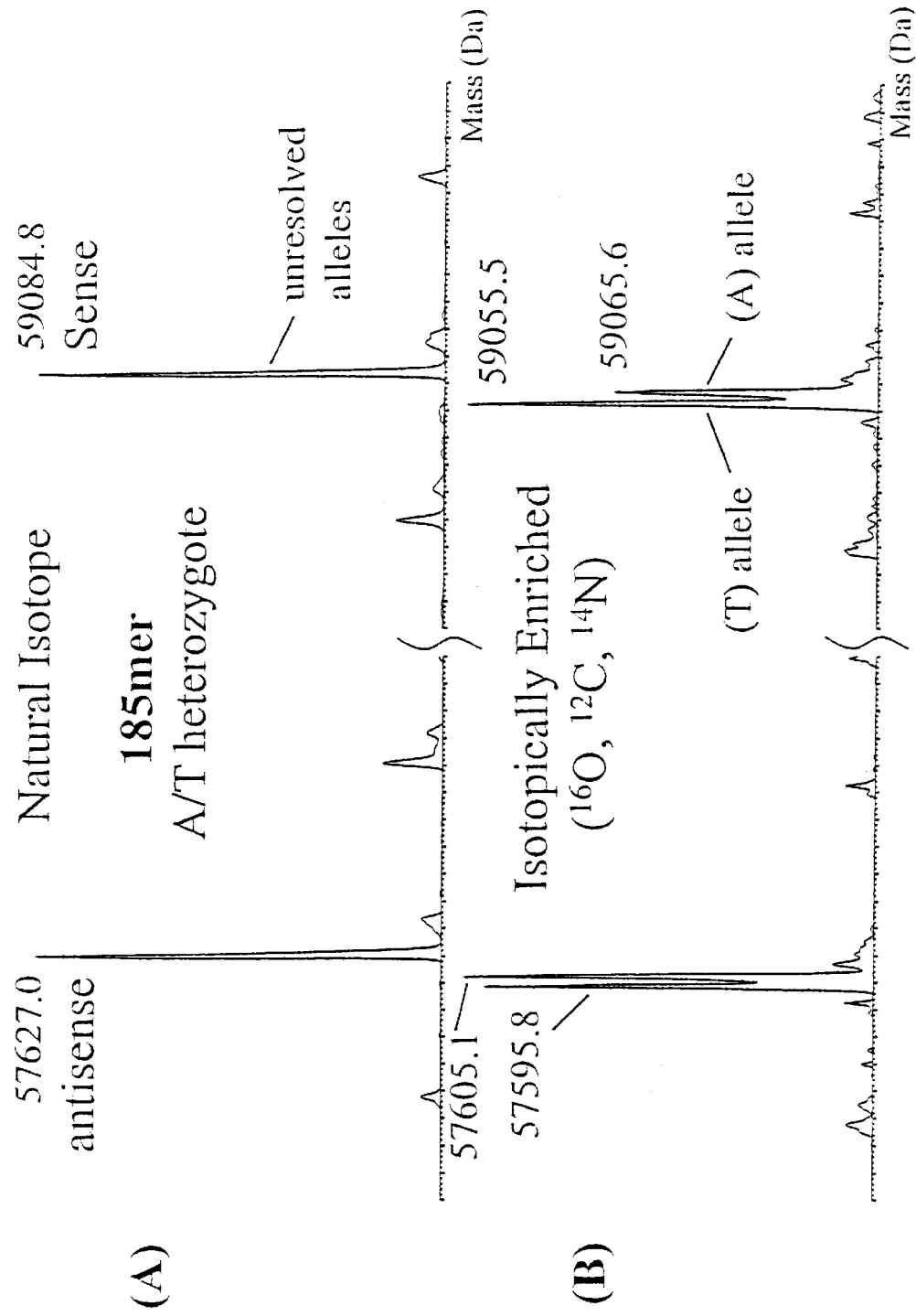
FIG. 5A shows the molecular mass spectrum of PCR products generated using natural-isotope dNTP's of a 185 nucleotide product of a region of the *adenomis polyposis coli* (APC) gene, in which a known A/T SNP occurs at gene sequence position 3920.
FIG. 5B is the molecular mass spectrum of isotopically enriched PCR products of the same sequence shown in FIG 5A.

FIG. 5 is a comparison of mass spectra showing the analysis of DNA products generated from PCR amplification of a region of the *adenomis polyposis coli* (APC) gene, in which a known A/T single nucleotide polymorphism (SNP) occurs at gene-sequence position 3920. The DNA sample analyzed is heterozygous (A/T) at the 3920 position. Genomic DNA was used for PCR template. The PCR products analyzed are 185 nucleotides in length (185 mer). FIG. 5A shows the molecular mass spectrum of PCR products generated using natural-isotope dNTP's; FIG. 5B is the molecular mass spectrum of isotopically enriched PCR products in which each DNA molecule is isotopically enriched to greater than 99.90 atom % in $^{12}C$, $^{16}O$ and $^{14}N$. Both sense and antisense DNA strands are shown in FIG. 5A and 5B. The alleles (A/T heterozygote) for each strand are mass spectrometrically unresolved for PCR products produced with natural isotopes (FIG. 5A); the alleles (A/T heterozygote) are separated and well resolved for isotopically enriched PCR products (FIG. 5B). FIG. 5 demonstrates that isotopic enrichment affords mass spectrometric resolution of A/T heterozygous alleles (A and T nucleotides differ in mass by 9 Da) in PCR products at least as large as 185 nucleotides.

Figure 6:
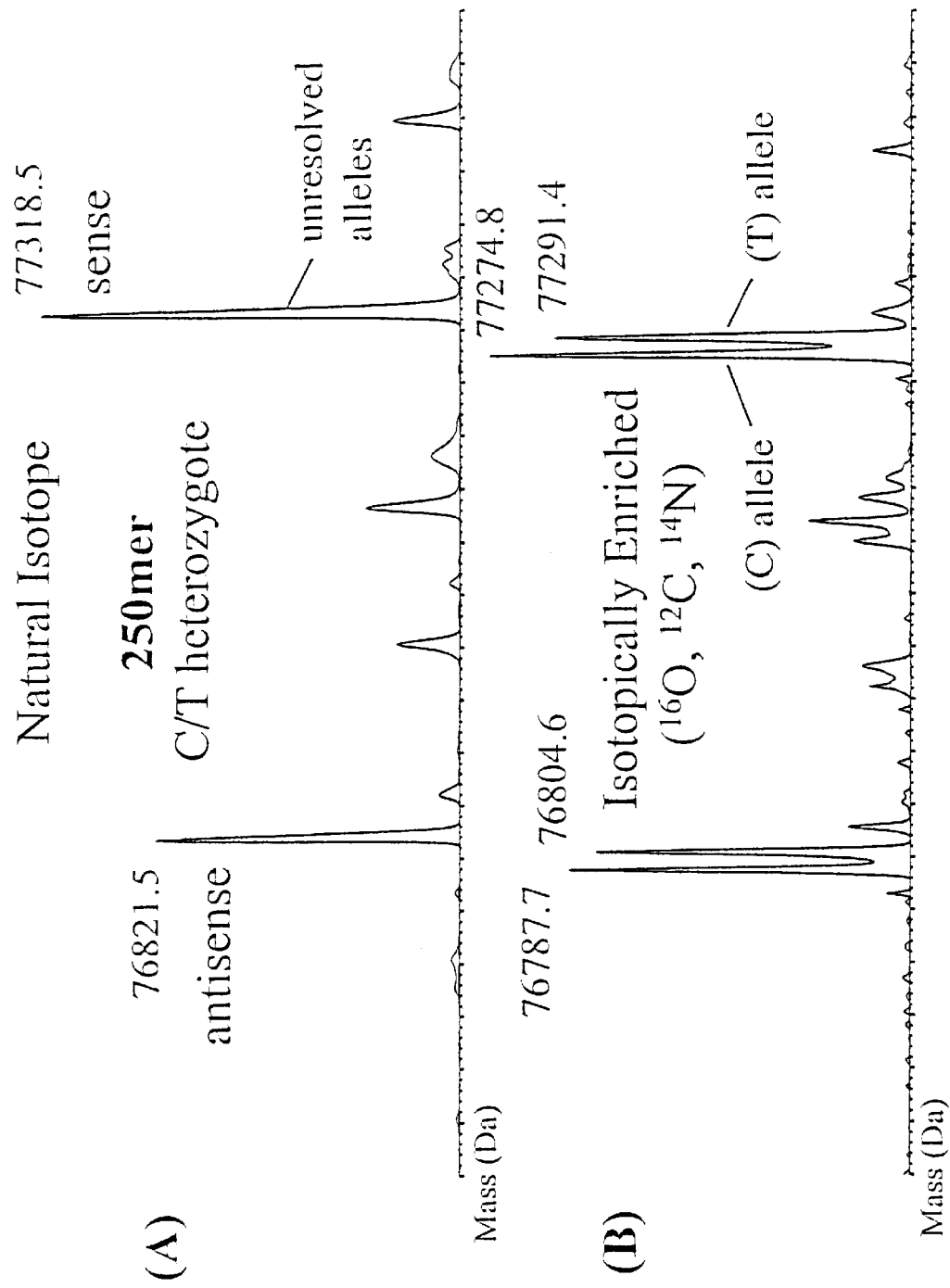
FIG. 6A shows the molecular mass spectrum of PCR products generated using natural-isotope dNTP's of a 250 nucleotide product of a region of the gap junction beta 2 (GJB2) gene, in which a previously unknown cytosyl (C)/ thymidyl (T) SNP in exon 8 was identified in this experiment.
FIG. 6B is the molecular mass spectrum of isotopically enriched PCR products of the same sequence shown in FIG. 6A.

FIG. 6 is a comparison of mass spectra showing the analysis of DNA products generated from PCR amplification of a region of the gap junction beta 2 (GJB2) gene. In this experiment a previously unknown C/T single nucleotide polymorphism (SNP) site in exon 8 of the gene was identified. The DNA sample analyzed is heterozygous (C/T). Genomic DNA was used for PCR template. The PCR products analyzed are 250 nucleotides in length (250mer). FIG. 6A shows the molecular mass spectrum of PCR products generated using natural-isotope dNTP's; FIG. 6B is the molecular mass spectrum of isotopically enriched PCR products in which each DNA molecule is isotopically enriched to greater than 99.90 atom % in $^{12}C$, $^{16}O$ and $^{14}N$. Both sense and antisense DNA strands are shown in FIG. 6A and 6B. For the sense strand, the molecular weight of C/T heterozygous alleles differ in mass by 15 Da; the complementary antisense strand G/A heterozygous alleles differ in mass by 16 Da (the calculated mass difference of G and A nucleotides is 16 Da). The alleles (C/T heterozygote) for each strand are mass spectrometrically unresolved for PCR products produced with natural isotopes (FIG. 6A); by comparison the alleles (C/T heterozygote) are separated and well resolved for isotopically enriched PCR products (FIG. 6B), for both the sense and anti-sense strands.

While in accordance with the patent statutes, description of the various embodiments and processing conditions have been provided, the scope of the invention is not to be limited thereto or thereby. Modifications and alterations of the present invention will be apparent to those skilled in the art without departing from the scope and spirit of the present invention.

What is claimed is:

1. A nucleoside monophosphate compound wherein all oxygen atoms comprised in said compound are enriched in an isotope of oxygen to an isotopic purity of at least 99.90 atom %.

2. A nucleoside monophosphate compound wherein all oxygen atoms comprised in said compound are enriched in $^{16}O$ isotope to an isotopic purity of at least 99.90 atom %.

3. A compound according to claim 2, wherein the isotopically enriched $^{16}O$ comprised in the nucleoside monophosphate is isotopically enriched to between about 99.90 atom % and about 99.99 atom % purity.

4. A compound according to claim 2, wherein the isotopically enriched $^{16}O$ comprised in the nucleoside monophosphate is isotopically enriched to between about 99.91 atom % and about 99.95 atom % purity.

5. A compound according to claim 2, wherein the isotopically enriched $^{16}O$ comprised in the nucleoside monophosphate is isotopically enriched to at least about 99.93 atom % purity.

6. A compound according to claim 2, wherein the isotopically enriched $^{16}O$ comprised in the nucleoside monophosphate is isotopically enriched to at least about 99.95 atom % purity.

7. A compound according to claim 1, wherein all carbon and nitrogen atoms comprised in said compound are enriched in an isotope selected from the group consisting of $^{12}C$ or $^{13}C$ and $^{14}N$ or $^{15}N$, and $^{13}C$ and $^{15}N$, wherein said compound is enriched to an isotopic purity of at least 99.90 atom % for all said combinations of isotopes.

8. A compound according to claim 2, wherein all carbon, nitrogen, and oxygen atoms comprised in said compound are enriched in $^{12}C$, $^{14}N$, and $^{16}O$ isotopes, respectively, to an isotopic purity of at least 99.90 atom %.

9. A compound according to claim 8, wherein each of said isotopically enriched chemical elements is isotopically enriched to between about 99.90 atom % and about 99.99 atom % purity.

10. A compound according to claim 8, wherein each of said isotopically enriched chemical elements is isotopically enriched to between about 99.91 atom % and about 99.95 atom % purity.

11. A compound according to claim 8, wherein each of said isotopically enriched chemical elements is isotopically enriched to at least about 99.93 atom % purity.

12. A nucleoside triphosphate compound wherein all oxygen atoms comprised in the nucleoside and alpha-phosphate moieties of said compound are enriched in an isotope of oxygen to an isotopic purity of at least 99.90 atom %.

13. A nucleoside triphosphate compound wherein all oxygen atoms comprised in the nucleoside and alpha-phosphate moieties of said compound are enriched in $^{16}O$ isotope to an isotopic purity of at least 99.90 atom %.

14. A compound according to claim 13, wherein all oxygen atoms comprised in the nucleoside and alpha-phosphate moieties of said nucleoside triphosphate are enriched in $^{16}O$ isotope to an isotopic purity of at least 99.93 atom %.

15. A compound according to claim 13, wherein said compound is derivatized with one or more methyl groups, wherein said methyl groups are enriched in $^{12}C$ isotope to an isotopic purity of at least 99.90 atom %.

16. A compound according to claim 13, wherein all carbon, nitrogen, and oxygen atoms comprised in the nucleoside and alpha-phosphate moieties of said nucleoside triphosphate are enriched in $^{12}C$, $^{14}N$, and $^{16}O$ isotopes, respectively, to an isotopic purity of at least 99.90 atom %.

17. A compound according to claim 16, wherein each isotopically enriched chemical element comprised in said nucleoside triphosphate is isotopically enriched to between about 99.90 atom % and about 99.99 atom % purity.

18. An isotopically enriched RNA or DNA wherein all oxygen atoms comprised in said RNA or DNA are enriched in an isotope of oxygen to an isotopic purity of at least 99.90 atom %.

19. An isotopically enriched RNA or DNA wherein all oxygen atoms comprised in said RNA or DNA are enriched in $^{16}O$ isotope to an isotopic purity of at least 99.90 atom %.

20. An isotopically enriched DNA or RNA according to claim 19, wherein said DNA or RNA comprises one or more nucleotides derivatized with one or more methyl groups, wherein said methyl groups are enriched in $^2C$ isotope to an isotopic purity of at least 99.90 atom %.

21. A method for the preparation of a nucleoside monophosphate in which all oxygen atoms comprised in said nucleoside monophosphate are enriched in an isotope of oxygen to an isotopic purity of at least 99.90 atom %, said method comprising the steps of:
    (a) producing DNA or RNA in an organism grown in a growth medium in which nutrients, reagents, solvents, and atmosphere are enriched in the same isotope of oxygen to an isotopic purity of at least 99.90 atom %;
    (b) isolating the isotopically enriched DNA or RNA; and
    (c) hydrolyzing said isotopically enriched DNA or RNA in water to produce nucleoside monophosphates, wherein said water is isotopically enriched in the same isotope of oxygen to at least 99.90 atom % purity.

22. A method according to claim 21, further comprising a step wherein an isotopically enriched nucleoside monophosphate, selected from the group consisting of adenosine monophosphate, guanosine monophosphate, thymidine monophosphate, cytidine monophosphate, uridine monophosphate, and modified nucleoside monophosphate, is isolated.

23. A method according to claim 21, wherein all oxygen atoms comprised in said nucleoside monophosphate are enriched in $^{16}O$ isotope to an isotopic purity of at least 99.90 atom %.

24. A method according to claim 21, further comprising a step wherein an isotopically enriched 2'-deoxy nucleoside monophosphate, selected from the group consisting of 2'-deoxy nucleoside monophosphates, and modified 2'-deoxy nucleoside monophosphates, is isolated.

25. A method according to claim 21, wherein said hydrolysis is accomplished with P1 endonuclease.

26. A method according to claim 21, further comprising a step wherein said nucleoside monophosphate is purified using reverse-phase and/or anion-exchange chromatography.

27. A method according to claim 21, wherein all carbon, nitrogen, and oxygen atoms comprised in said nucleoside monophosphate are enriched in $^{12}C$, $^{14}N$, and $^{16}O$ isotopes, respectively, and wherein said growth medium of step (a) is enriched in $^{12}C$, $^{14}N$, and $^{16}O$ isotopes to an isotopic purity of at least 99.90 atom %.

28. A method for the preparation of a nucleoside triphosphate in which all oxygen atoms comprised in the nucleoside and alpha-phosphate moieties of said nucleoside triphosphate are enriched in the same isotope of oxygen to an isotopic purity of at least 99.90 atom %, said method comprising the steps of:
    (a) producing DNA or RNA in an organism grown in a growth medium in which the nutrients, reagents, solvents, and atmosphere are enriched in the same isotope of oxygen to an isotopic purity of at least 99.90 atom %;
    (b) isolating the isotopically enriched DNA or RNA;
    (c) hydrolyzing the isotopically enriched DNA or RNA in water to produce nucleoside monophosphates, wherein said water has been enriched in the same isotope of oxygen to an isotopic purity of at least 99.90 atom %; and
    (d) phosphorylating the nucleoside monophosphates using one or more nucleoside kinasing enzymes to produce a nucleoside triphosphate.

29. A method according to claim 28, wherein all oxygen atoms comprised in the nucleoside and alpha-phosphate moieties of said nucleoside triphosphate are enriched in $^{16}O$ isotope to an isotopic purity of at least 99.90 atom %.

30. A method according to claim 29, wherein said nucleoside kinasing enzyme is selected from the group consisting of pyruvate kinase, guanylate kinase, nucleoside monophosphate kinase, myokinase, thymidylate kinase and an *E. coli* kinasing enzyme fraction.

31. A method for the preparation of RNA or DNA, wherein all oxygen atoms comprised in said RNA or DNA is enriched in an isotope of oxygen to an isotopic purity of at least 99.90 atom %, said method comprising the steps of:
    (a) producing RNA or DNA in an organism grown in a growth medium in which the nutrients, reagents, solvents and atmosphere are enriched in same isotope of oxygen to an isotopic purity of at least 99.90 atom %; and
    (b) isolating isotopically enriched RNA or DNA.

32. A method according to claim 31, wherein all oxygen atoms comprised in said RNA or DNA are enriched in $^{16}O$ isotope to an isotopic purity of at least 99.90 atom %.

33. A method according to claim 32, wherein said RNA is selected from the group consisting of mRNA, tmRNA, tRNA and rRNA.

34. A method of synthesizing an isotopically enriched DNA or RNA oligonucleotide comprising using a technique selected from the group consisting of polymerase chain reaction (PCR) amplification, reverse-transcriptase polymerase chain reaction (RT-PCR) amplification, oligo-ligation amplification (OLA), rolling-circle amplification, and single-nucleotide primer extension reaction (SNuPE), wherein nucleotide, nucleoside triphosphate, or oligonucleotide reagents used for a select synthesis technique are enriched in an isotope of oxygen, wherein all oxygen atoms comprised in said reagents are enriched in an isotope of oxygen to an isotopic purity of at least 99.90 atom %, and said nucleoside triphosphate comprises beta- and gamma-phosphate groups that are not necessarily isotopically enriched.

35. A method for determining the mass of an oligonucleotide, wherein all oxygen atoms comprised in said oligonucleotide are enriched in an isotope of oxygen, said method comprising the steps of:
    (a) making an oligonucleotide, wherein all oxygen atoms comprised in said oligonucleotide are enriched in an isotope of oxygen to an isotopic purity of at least 99.90 atom %; and
    (b) determining the mass of said isotopically enriched oligonucleotide using mass spectrometry.

36. A method according to claim 35, all oxygen atoms comprised in said oligonucleotide are enriched in $^{16}O$ isotope, said method comprising the steps of:
    (a) making an oligonucleotide, wherein all oxygen atoms comprised in said oligonucleotide are enriched in $^{16}O$ isotope to an isotopic purity of at least 99.90 atom %; and
    (b) determining the mass of said isotopically enriched oligonucleotide using mass spectrometry.

37. A method according to claim 36, wherein said method further comprises the steps of:
    (a) producing DNA or RNA, wherein all oxygen atoms comprised in said DNA or RNA are enriched in $^{16}O$ isotope to an isotopic purity of at least 99.90 atom %, in which said DNA or RNA is derived from organisms grown in a growth medium wherein all oxygen atoms comprised in the nutrients, reagents, solvents, and atmosphere are enriched in $^{16}O$ isotope to an isotopic purity of at least 99.90 atom %;
    (b) hydrolyzing the isotopically enriched DNA or RNA in $^{16}O$-enriched water;
    (c) phosphorylating the isotopically enriched nucleoside monophosphates; and
    (d) using the resulting nucleoside triphosphates in a polymerase chain reaction amplification to prepare a DNA or RNA oligonucleotide, wherein all oxygen atoms comprised in said DNA or RNA are enriched in $^{16}O$ isotope to an isotopic purity of at least 99.90 atom %.

38. A method according to claim 37, wherein said oligonucleotide comprises between about 100 nucleotides and about 600 nucleotides.

39. A method according to claim 37, wherein the oligonucleotide comprises between about 100 nucleotides and about 1000 nucleotides.

40. A method according to claim 35, wherein said mass spectrometry is used in conjunction with electrospray ionization or matrix-assisted laser desorption ionization.

41. A method according to claim 37, wherein said method further comprises the steps of:
    (a) producing DNA or RNA, wherein all carbon, nitrogen, and oxygen atoms comprised in said DNA or RNA are enriched in $^{12}C$, $^{14}N$, and $^{16}O$ isotopes, respectively, to an isotopic purity of at least 99.90 atom %, in which said DNA or RNA is derived from organisms grown in a growth medium, wherein carbon, nitrogen, and oxygen atoms comprised in the nutrients, reagents, solvents, and atmosphere are enriched in $^{12}C$, $^{14}N$ and $^{16}O$ isotopes, respectively, to an isotopic purity of at least 99.90 atom %;
    (b) hydrolyzing the isotopically enriched DNA or RNA in $^{16}O$ enriched water;
    (c) phosphorylating the isotopically enriched nucleoside monophosphates;
    (d) using the resulting nucleoside triphosphates in a polymerase chain reaction (PCR) amplification to prepare a DNA or RNA oligonucleotide, wherein all carbon, nitrogen, and oxygen atoms comprised in said oligonucleotide are enriched in $^{12}C$, $^{14}N$, and $^{16}O$ isotopes to an isotopic purity of at least 99.90 atom %.

42. A method according to claim 37, wherein an oligonucleotide is generated by PCR from a DNA or RNA template that may contain no genetic variants or may contain at least one known genetic variant selected from the group consisting of single-nucleotide polymorphisms (SNPs), deletions, insertions, and tandem repeat regions, wherein a genetic variant in the tandem repeat regions may also include a one or more SNPs, one or more nucleotide deletions, or one or more nucleotide insertions; wherein said method comprises the steps of:
    (a) making an oligonucleotide, wherein all oxygen atoms comprised in said oligonucleotide are enriched in $^{16}O$ isotope to an isotopic purity of at least 99.90 atom %; and
    (b) determining the mass of said isotopically enriched oligonucleotide using mass spectrometry.

43. A method of identifying a known genetic variant, nucleic acid, and/or nucleic acid structural modification in an oligonucleotide, wherein all oxygen atoms comprised in said oligonucleotide are enriched in an isotope of oxygen to an isotopic purity of at least 99.90 atom %, said method comprising the steps of:
    (a) making an oligonucleotide, wherein all oxygen atoms comprised in said oligonucleotide enriched in an isotope of oxygen to an isotopic purity of at least 99.90 atom %; and
    (b) determining the mass of said isotopically enriched oligonucleotide using mass spectrometry;

wherein said genetic variants are selected from the group consisting of single-nucleotide polymorphisms, deletions, insertions, and tandem repeat regions.

44. A method of identifying an unknown genetic variant, nucleic acid, and/or nucleic acid structural modification in an oligonucleotide, wherein all oxygen atoms comprised in said oligonucleotide are enriched in an isotope of oxygen to an isotopic purity of at least 99.90 atom %, wherein said method comprising the steps of:
   (a) making an oligonucleotide, wherein all oxygen atoms comprised in said oligonucleotide are enriched in an isotope of oxygen to an isotopic purity of at least 99.90 atom %; and
   (b) determining the mass of said isotopically enriched oligonucleotide using mass spectrometry;
   wherein said genetic variants are selected from the group consisting of single-nucleotide polymorphisms, deletions, insertions, and tandem repeat regions.

45. A compound according to claim 13, wherein all oxygen atoms comprised in the nucleoside and alpha-phosphate moieties of said nucleoside triphosphate are enriched in $^{16}$O isotope to an isotopic purity between about 99.90 atom % and about 99.99 atom %.

46. A compound according to claim 16, wherein all carbon, nitrogen, and oxygen atoms comprised in the nucleoside and alpha-phosphate moieties of said nucleoside triphosphate are enriched in $^{12}$C, $^{14}$N, and $^{16}$O isotopes, respectively, to an isotopic purity of at least 99.93 atom %.

47. An isotopically enriched RNA or DNA according to claim 19, wherein all oxygen atoms comprised in said RNA or DNA are enriched in $^{16}$O isotope to an isotopic purity between about 99.90 atom % and 99.99 atom %.

48. An isotopically enriched RNA or DNA according to claim 19, wherein all oxygen atoms comprised in said RNA or DNA are enriched in $^{16}$O isotope to an isotopic purity of at least 99.93 atom %.

49. An isotopically enriched RNA or DNA according to claim 19, wherein all carbon, nitrogen, and oxygen atoms comprised in said RNA or DNA are enriched in $^{12}$C, $^{14}$N, and $^{16}$O isotopes, respectively, to an isotopic purity of at least 99.90 atom %.

50. An isotopically enriched RNA or DNA according to claim 19, wherein all carbon, nitrogen, and oxygen atoms comprised in said RNA or DNA are enriched in $^{12}$C, $^{14}$N, and $^{16}$O isotopes, respectively, to an isotopic purity of at least 99.93 atom %.

51. An isotopically enriched RNA or DNA according to claim 19, wherein all carbon, nitrogen, and oxygen atoms comprised in said RNA or DNA are enriched in $^{12}$C, $^{14}$N, and $^{16}$O isotopes, respectively, to an isotopic purity between about 99.90 atom % and 99.99 atom %.

52. A method according to claim 28, wherein all oxygen atoms comprised in the nucleoside and alpha-phosphate moieties of said nucleoside triphosphate are enriched in $^{16}$O isotope to an isotopic purity of at least 99.93 atom %.

53. A method according to claim 28, wherein all carbon, nitrogen, and oxygen atoms comprised in the nucleoside and alpha-phosphate moieties of said nucleoside triphosphate are enriched in $^{12}$C, $^{14}$N, and $^{16}$O isotopes, respectively, to an isotopic purity of at least 99.90 atom %.

54. A method according to claim 28, wherein all carbon, nitrogen, and oxygen atoms comprised in the nucleoside and alpha-phosphate moieties of said nucleoside triphosphate are enriched in $^{12}$C, $^{14}$N, and $^{16}$O isotopes, respectively, to an isotopic purity of at least 99.93 atom %.

55. A method according to claim 32, wherein all carbon, nitrogen, and oxygen atoms comprised in said RNA or DNA are enriched in $^{12}$C, $^{14}$N, and $^{16}$O isotopes, respectively, to an isotopic purity of at least 99.90 atom %.

56. A method according to claim 32, wherein all carbon, nitrogen, and oxygen atoms comprised in said RNA or DNA are enriched in $^{12}$C, $^{14}$N, and $^{16}$O isotopes, respectively, to an isotopic purity of at least 99.93 atom %.

57. A method according to claim 34, wherein all oxygen atoms comprised in the nucleoside and alpha-phosphate moieties of said nucleoside triphosphate reagents are enriched in $^{16}$O isotopic to an isotopic purity of at least 99.90 atom %.

58. A method according to claim 34, wherein all carbon, nitrogen, and oxygen atoms comprised in the nucleoside and alpha-phosphate moieties of said nucleoside triphosphate reagents are enriched in $^{12}$C, $^{14}$N, and $^{16}$O isotopes, respectively, to an isotopic purity of at least 99.90 atom %.

59. A method according to claim 36, wherein said oligonucleotide is produced that is enriched in $^{12}$C, $^{14}$N, and $^{16}$O isotopes to an isotopic purity of at least 99.90 atom %, wherein said method comprises the steps of:
   (a) making an oligonucleotide, wherein all carbon, nitrogen, and oxygen atoms comprised in the nucleoside and alpha-phosphate moieties of said nucleoside triphosphate reagents are enriched in $^{12}$C, $^{14}$N, and $^{16}$O isotopes, respectively, to an isotopic purity of at least 99.90 atom %; and
   (b) determining the mass of said isotopically enriched oligonucleotide using mass spectrometry.

60. A method according to claim 59, wherein said oligonucleotide is comprised of $^{12}$C, $^{14}$N, $^{16}$O, $^{1}$H, and $^{31}$P isotopes, wherein all hydrogen atoms ($^{1}$H isotope) are at about 99.985 atom % purity and all phosphorus atoms ($^{31}$P isotope) are at about 100 atom % isotopic purity, such that all atoms of all constituent elements comprising said oligonucleotide are at isotopic purities of at least 99.90 atom %, said method comprising the steps of:
   (a) making an oligonucleotide, wherein all carbon, nitrogen, oxygen, hydrogen, and phosphorus atoms comprised in said oligonucleotide are isotopically pure to at least 99.90 atom % in the isotopes of $^{12}$C, $^{14}$N, $^{16}$O, $^{1}$H, and $^{31}$P, respectively; and
   (b) determining the mass of said isotopically enriched oligonucleotide using mass spectrometry.

61. A method according to claim 59, wherein said oligonucleotide comprises between about 100 nucleotides and about 600 nucleotides.

62. A method according to claim 59, wherein said oligonucleotide comprises between about 100 nucleotides and about 1000 nucleotides.

63. A method according to claim 59, wherein said mass spectrometry is used in conjunction with electrospray ionization or matrix-assisted laser desorption ionization.

64. A method according to claim 37, wherein said oligonucleotide generated from a DNA or RNA template contains at least one unknown genetic variant selected from the group consisting of single-nucleotide polymorphisms (SNPs), deletions, insertions, and tandem repeat regions, wherein a genetic variant in the tandem repeat regions may also include one or more SNPs, one or more nucleotide deletions, or one or more nucleotide insertions; wherein said method comprises the steps of:
   (a) making an oligonucleotide, wherein all oxygen atoms comprised in said oligonucleotide are enriched in $^{16}$O isotope to an isotopic purity of at least 99.90 atom %; and
   (b) determining the mass of said isotopically enriched oligonucleotide using mass spectrometry.

65. A method according to claim 41, wherein an oligonucleotide is generated by PCR from a DNA or RNA template that may contain no genetic variants or may contain at least one known genetic variant selected from the group consisting of single-nucleotide polymorphisms (SNPs), deletions, insertions, and tandem repeat regions, wherein a genetic variant in the tandem repeat regions may also include one or more SNPs, one or more nucleotide deletions, or one or more nucleotide insertions; wherein said method comprises the steps of:
- (a) making an oligonucleotide, wherein all carbon, nitrogen, and oxygen atoms comprised in said oligonucleotide are enriched in $^{12}C$, $^{14}N$, and $^{16}O$ isotopes, respectively, to an isotopic purity of at least 99.90 atom %; and
- (b) determining the mass of said isotopically enriched oligonucleotide using mass spectrometry.

66. A method according to claim 41, wherein an oligonucleotide is generated DNA or RNA template and contains at least one unknown genetic variant selected from the group consisting of single-nucleotide polymorphisms (SNPs), deletions, insertions, and tandem repeat regions, wherein a genetic variant in the tandem repeat regions may also include one or more SNPs, one or more nucleotide deletions, or one or more nucleotide insertions; wherein said method comprises the steps of:
- (a) making an oligonucleotide, wherein all carbon, nitrogen, and oxygen atoms comprised in said oligonucleotide are enriched in $^{12}C$, $^{14}N$, and $^{16}O$ isotopes, respectively, to an isotopic purity of at least 99.90 atom %; and
- (b) determining the mass of said isotopically enriched oligonucleotide using mass spectrometry.

67. A method of identifying a known genetic variant, nucleic acid, and/or nucleic acid structural modification in an oligonucleotide, the method comprising the steps of:
- (a) making an oligonucleotide, wherein all oxygen atoms comprised in said oligonucleotide are enriched in $^{16}O$ isotope to an isotopic purity of at least 99.90 atom %; and
- (b) determining the mass of said isotopically enriched oligonucleotide using mass spectrometry;

wherein said genetic variant is selected from the group consisting of single-nucleotide polymorphisms, deletions, insertions, and tandem repeat regions.

68. A method of identifying a known genetic variant, nucleic acid, and/or nucleic acid structural modification in an oligonucleotide, the method comprising the steps of:
- (a) making an oligonucleotide, wherein all carbon, nitrogen, and oxygen atoms comprised in said oligonucleotide are enriched in $^{12}C$, $^{14}N$, and $^{16}O$ isotopes, respectively, to an isotopic purity of at least 99.90 atom %; and
- (b) determining the mass of said isotopically enriched oligonucleotide using mass spectrometry;

wherein said genetic variant is selected from the group consisting of single-nucleotide polymorphisms, deletions, insertions, and tandem repeat regions.

69. A method of identifying an unknown genetic variant, nucleic acid, and/or nucleic acid structural modification in an oligonucleotide, the method comprising the steps of:
- (a) making an oligonucleotide, wherein all oxygen atoms comprised in said oligonucleotide are enriched in $^{16}O$ isotope to an isotopic purity of at least 99.90 atom %; and
- (b) determining the mass of said isotopically enriched oligonucleotide using mass spectrometry;

wherein said genetic variant is selected from the group consisting of single-nucleotide polymorphisms, deletions, insertions, and tandem repeat regions.

70. A method of identifying an unknown genetic variant, nucleic acid, and/or nucleic acid structural modification in an oligonucleotide, the method comprising the steps of:
- (a) making an oligonucleotide, wherein all carbon, nitrogen, and oxygen atoms comprised in said oligonucleotide are enriched in $^{12}C$, $^{14}N$, and $^{16}O$ isotopes, respectively, to an isotopic purity of at least 99.90 atom %; and
- (b) determining the mass of said isotopically enriched oligonucleotide using mass spectrometry;

wherein said genetic variant is selected from the group consisting of single-nucleotide polymorphisms, deletions, insertions, and tandem repeat regions.

71. A method according to claim 41, the oligonucleotide comprises between about 100 nucleotides and about 600 nucleotides.

72. A method according to claim 41, wherein the oligonucleotide comprises between about 100 nucleotides and about 1000 nucleotides.

* * * * *

UNITED STATES PATENT AND TRADEMARK OFFICE
CERTIFICATE OF CORRECTION

PATENT NO. : 6,734,294 B2
DATED : May 11, 2004
INVENTOR(S) : Chad C. Nelson and Lesa M. Nelson It is certified that error appears in the above-identified patent and that said Letters Patent is hereby corrected as shown below:

Title page,
Item [54], Title, before "THEREOF" change "PURIFICATION" to -- USES --
Item [56], References Cited, OTHER PUBLICATIONS, "Batey R.T. et al.", reference, change "Researchvol." to -- Research, vol. --
"Chen X. et al., *A PCR Based Method*", reference, change "*Letter*," to -- *Letters*, 436, --

Column 1
Line 3, after "AND" change "PURIFICATION" to -- USES --
Line 19, change "spectrometry." to -- spectrometry and genetics. --
Line 48, after "acids." insert -- One aspect of the invention describes producing a nucleic acid molecule that is comprised of all atoms of all elements in a single isotopic species (*i.e.* $^{12}$C, $^{14}$N, $^{16}$O, $^{1}$H, and $^{31}$P) at very high isotopic purity (*i.e.* at least 99.90 atom % for each elemental isotope). --
Line 50, before "nucleic" insert -- isotopically enriched --
Line 53, change "(PCRs)" to -- (PCR) --

Column 2,
Line 4, change "$^{12}$C" to -- $^{13}$C --
Line 7, change "$^{16}$O" to -- $^{16}$O --
Lines 16 and 17, remove "In one aspect, the nucleotide is enriched in an isotope of oxygen"
Lines 28 and 29, after "enriched in" change "an isotope of oxygen." to -- $^{12}$C, $^{14}$N, and $^{16}$O at all carbon, nitrogen, and oxygen atoms, respectively, at a purity of at least 99.90 atom %. --
Line 40, change "deoxynucleotides (dNTP's)" to -- deoxynucleosides (dNTPs) --
Line 49, after "known" insert -- genetic variant of a heterozygote --
Line 49, after "A/T" change "(adenosyl/thymidyl)" to
-- (deoxyadenylate/deoxythymidylate) --
Lines 57 and 58, change "126 nucleotide" to -- 126-nucleotide --
Line 59, after "known" insert -- genetic variant of a heterozygote --

Column 3,
Line 4, after "known" insert --genetic variant of a heterozygote --
Line 7, change "FIG 5A" to -- FIG. 5A --
Line 13, change "cytosyl (C)/ thymidyl (T)" to -- genetic variant of a heterzygote C/T (deoxycytidylate/deoxythymidylate) --
Line 18, change "$^{16}$O and $^{14}$N." to -- $^{14}$N, and $^{16}$O. --

UNITED STATES PATENT AND TRADEMARK OFFICE
CERTIFICATE OF CORRECTION

PATENT NO. : 6,734,294 B2
DATED : May 11, 2004
INVENTOR(S) : Chad C. Nelson and Lesa M. Nelson It is certified that error appears in the above-identified patent and that said Letters Patent is hereby corrected as shown below:

Column 4,
Line 12, change "can be found in can be found in" to -- can be found in --
Line 34, before ""natural abundance"" insert -- phrase "naturally-occurring" or --
Line 46, before "The phrase" insert -- For purposes of this invention, the phrase "isotopically enriched" may be used interchangeably with the phrases "isotopic enrichment", "enrichment", or "enriched". --
Line 48, change "one or more constituent atoms" to -- all atoms of a chemical element of a molecule, to at least 99.90 atom % purity. --
Line 51, change "$_{16}O$" to -- $^{16}O$ --
Line 52, before "$^{18}O$" change "and" to -- or --

Column 5,
Lines 1-6, remove paragraph beginning with "The term "purity" refers" and ending with "98.9 atom % purity." and insert the following paragraph:
-- The terms "isotopic purity", "purity", or "atom % purity" may be used interchangeably and refer to the relative abundance of an isotope compared to the other stable isotopes of an element. For instance, the element of carbon exists naturally as two stable isotopes ($^{12}C$ and $^{13}C$), in which $^{12}C$ is present at 98.9 atom % relative abundance (or "isotopic purity"), while the $^{13}C$ isotope is present naturally at 1.1 atom % relative "isotopic purity". --
Line 19, before "oligonucleotides" insert -- nucleic acids or --
Lines 43-45, remove "The terms "minimal growth media" and "growth medium" refer to media that provide the nutients, salts, water and atmosphere needed by an organism for growth." and replace with -- The terms "media" or "growth media" or "growth medium" or "minimal growth media" may be used interchangeably herein and are used to collectively describe the nutrients, reagents, solvents, salts, water, atmosphere, and other components required for cell growth. --
Line 54, change "growth factors" to -- growth factors, nutrients, reagents, and solvents. --
Line 65, change "supplied" to -- used --

Column 6,
Lines 42-44, remove paragraph beginning with "The term "isolating" refers to" and ending with "90 % higher purity."
Between lines 61 and 62, insert the following paragraph:
-- With increasing molecular weight, a DNA molecule (consisting of naturally-occurring isotope abundances) is comprised of an increasingly broad isotope distribution, resulting in a correspondingly broad mass spectrometric peak width. Moreover, with naturally-abundant isotopes, an inherent mass spectrometric limitation is reached whereby two different DNA molecules with a relatively-small mass difference can still be resolved and accurately measured (*e.g.* genetic variants). --

UNITED STATES PATENT AND TRADEMARK OFFICE
CERTIFICATE OF CORRECTION

PATENT NO. : 6,734,294 B2
DATED : May 11, 2004
INVENTOR(S) : Chad C. Nelson and Lesa M. Nelson It is certified that error appears in the above-identified patent and that said Letters Patent is hereby corrected as shown below:

Column 6 (cont'd),
Line 63, after "enrichment of" insert -- an isotope of --
Line 64, after "oxygen" insert -- (*e.g.* $^{16}O$) --
Line 66, change "resolve" to -- mass spectrometrically resolve small mass differences between --
Line 67, after "increased" change "by" to -- through combined --

Column 7,
Line 1, before "such as," insert -- as well, --
Line 1, remove "for example,"
Line 2, before "isotopic" remove "possible"
Line 3, before "molecular" change "for" to -- of --
Line 3, after "creates" insert -- correspondingly --
Line 4, after "ability to" insert -- mass spectometrically --
Line 5, change "oligonucleotides. As" to -- oligonucleotides with small mass differences. Through isotopic enrichment of all oxygen, carbon, and nitrogen atoms in DNA to at least 99.90 atom % purity, genetic variants, such as an A/T heterozygote SNP (*i.e.* Da mass difference), can be mass spectrometrically resolved in large DNA molecules. Moreover, as --
Line 6, after "above" change "99.9" to -- 99.90 --
Line 9, change "Since" to -- As a result of isotopic enrichment of all oxygen, carbon, and nitrogen atoms, with $^{16}O$, $^{12}C$, and $^{14}N$, respectively, --
Line 10, after "distribution" change "and, thus," to -- yielding a --
Line 11, after "width," change "there is" to -- with --
Line 18, before "tandem" remove "short"
Line 19, remove "(STRs)"
Line 32, change "150" to -- 100 --
Line 58, after "at least" change "99.9" to -- 99.90 --

Column 8,
Line 36, after "at least" change "99.9" to -- 99.90 --

Column 9,
Line 2, after "at least" change "99.9" to -- 99.90 --
Line 30, before "or" insert -- in all elements, --
Line 31, before "isotopically" remove "selectively"
Line 31, change "enriched, as required" to -- enriched in one or more chemical elements, as required --

UNITED STATES PATENT AND TRADEMARK OFFICE
CERTIFICATE OF CORRECTION

PATENT NO. : 6,734,294 B2
DATED : May 11, 2004
INVENTOR(S) : Chad C. Nelson and Lesa M. Nelson It is certified that error appears in the above-identified patent and that said Letters Patent is hereby corrected as shown below:

Column 9 (cont'd),
Line 34, change "enrichment should" to -- enrichment, such as $^{16}O$ for oxygen and $^{14}N$ for nitrogen (as in the nutrient ammonium sulfate (($^{14}NH_4)_2$ S $^{16}O_4$)), should --
Line 34, after "contain" change "that chemical element in" to -- chemical elements enriched to --
Line 35, before "atom %" change "99.9" to -- 99.90 --
Line 40, change "99.95 atom % pure to decrease chance or trace-level contamination from" to -- 99.95 % chemically pure to minimize possible incorporation of undesired elements from tracelevel --
Line 43, after "example" insert -- contaminants containing --
Line 43, before "nitrogen" change "and" to -- or --

Column 10,
Line 56, change "Isotopically enriched" to -- Isotopically-enriched --
Line 64, change "isotopically enriched" to -- isotopically-enriched --

Column 11,
Line 4, change "triphosphate" to -- triphosphates --
Line 13, before "selectively" insert -- additionally --
Line 14, before "Incorporation" change "mass." to -- mass relative to other nucleotides. --
Line 23, change "nucleotides to 3 Da." to -- nucleotides from 9 Da to 12 Da. --
Line 24, after "ability to" change "resolve an A/T heterozygote mass spectrometrically" to -- mass spectrometrically resolve DNA molecules with an A/T nucleotide compositional difference --
Line 27, after "A/T" change "difference." to -- difference in genetic alleles or A/T SNP heterozygous DNA molecules. --
Line 28, after "derivative of" change "a" to -- an isotopically enriched --
Line 30, before "isotopically" insert -- similarly --
Line 46, after "both" change "A" to -- deoxyadenylate (A) --
Line 47, change "guanosyl" to -- deoxyguanylate --
Line 58, change "methylation" to -- functional group --
Line 65, before "embodiment" change "One" to -- For the $^{15}N$ mass tag method, for example, DNA or RNA is isotopically enriched in $^{12}C$, $^{15}N$ and $^{16}O$ isotopes, wherein the DNA or RNA is isotopically enriched to at least 99.90 atom % in all of these elemental isotopes. For the $^{12}CH_3$ methylation mass tag, one --

UNITED STATES PATENT AND TRADEMARK OFFICE
CERTIFICATE OF CORRECTION

PATENT NO.     : 6,734,294 B2
DATED          : May 11, 2004
INVENTOR(S)    : Chad C. Nelson and Lesa M. Nelson It is certified that error appears in the above-identified patent and that said Letters Patent is hereby corrected as shown below:

Column 12,
Line 2, after "RNA" insert -- is isotopically enriched to at least 99.90 atom % purity and --
Line 5, change "$^{12}$C." to -- $^{12}$C to at least 99.90 atom % purity. --
Line 11, after "guanosine triphosphate," insert -- cytidine triphosphate --
Line 14, before "nucleoside" insert -- a --
Line 19, change "$^{12}$C." to -- $^{12}$C to at least 99.90 atom % purity. --
Line 28, before "water" insert -- in --
Line 29, before "oxygen" insert -- of --
Line 39, before "and $^{12}$C," insert -- $^{16}$O and $^{12}$C; --

Column 13,
Line 9, after "DNA" insert -- or RNA --
Line 16, change "used (prior to adding the P1 enzyme)," to -- hydrolyzed, --
Line 17, change "boiled," to -- boiled (prior to adding the P1 enzyme), --
Line 39, change "anion exchange" to -- anion-exchange --
Lines 42 and 43, change "anion exchange" to -- anion-exchange --
Line 45, change "HPLC" to -- (HPLC) --
Line 52, after "extraction" insert -- (SPE) --
Line 59, change "eluted over" to -- loaded onto --
Line 60, after "extraction" insert -- (SPE) --
Line 63, after "TEABC" insert -- (triethylammonium bicarbonate) --
Line 64, after "HPLC-grade" insert -- water --

Column 14,
Lines 1 and 2, change "introducing multiple oxygen isotopes." to -- exchanging out incorporated $^{16}$O isotopes with other isotopes of oxygen. --
Line 67, change "phosphate donating" to -- phosphate-donating --

Column 16,
Line 7, after "triphosphates," change "like" to -- the --
Lines 11 and 12, change "at least one" to -- a C18 reverse-phase --
Line 15, change "the anion exchange" to -- anion-exchange --
Line 15, after "chromotography" remove "employs"
Line 16, after "columns" insert -- are employed --
Line 30, after "at least" change "99.9" to -- 99.90 --

UNITED STATES PATENT AND TRADEMARK OFFICE
CERTIFICATE OF CORRECTION

PATENT NO. : 6,734,294 B2
DATED : May 11, 2004
INVENTOR(S) : Chad C. Nelson and Lesa M. Nelson It is certified that error appears in the above-identified patent and that said Letters Patent is hereby corrected as shown below:

Column 17,
Line 17, before "in organisms" remove "or RNA"
Line 23, after "enriched" change "nucleoside" to -- deoxynucleoside --
Line 24, change "nucleoside triphophate" to -- deoxynucleoside triphophate (dNTPs) --
Line 36, change "oligonucleotide" to -- isotopically enriched oligonucleotide is prepared by PCR amplification using DNA as PCR template, in which the DNA. --
Lines 38 and 39, change "short-tandem" to -- tandem --
Line 40, change "oligonucleotide" to -- isotopically enriched oligonucleotide is prepared by PCR amplification using DNA as PCR template, in which the DNA --
Line 42, change "short-tandem" to -- tandem --

Column 18,
Line 6, before "tandem" remove "short"
Line 16, change "short-tandem" to -- tandem --
Line 17, before "method" insert -- a --
Line 26, change "short-tandem repeat regions." to -- tandem repeat regions in DNA or RNA: --
Line 62, after "(Isotec)." insert -- The pH of the media may be adjusted to about pH 7.0 with 0.5 M sodium hydroxide ($^{16}O$>99.95 atom %; Isotec). --
Line 63, before "$E.$ $coli.$" insert -- A methylation-deficient strain of $E.$ $coli$ that contains lam(-) and/or dam(-) mutations (GM33, $E$ $coli$ Genetic Stock Center, Yale University) was used in the minimal-growth media to generate isotopically enriched nucleic acids. --
Line 64, before "Five" change "follows" to -- follows: --
Line 64, after "millimeters of the" insert -- isotopically-enriched minimal --
Lines 66 and 67, remove "(grown under rich media and natural isotope reagents and conditions)"

Column 19,
Line 2, change "sample was" to -- cells were --
Line 9, after "oxygen" insert -- gas --
Line 9, change "(16O)" to -- ($^{16}O$ --
Line 10, change "purity)" to -- purity; Isotec) --
Line 56, after "Nucleosides" insert -- (dNTPs) --
Line 58, change "the extracted DNA" to -- hydrolysis of the extracted DNA into nucleoside monophosphates and subsequent phosphorylation of the nucleoside monophophates --
Line 60, before "to prevent" insert -- in order to incorporate an $^{16}O$ atom during hydrolysis of DNA, such that the alpha-phosphate moiety was entirely isotopically enriched in $^{16}O$, and also --
Line 61, after "natural" remove "isotopic abundance"

UNITED STATES PATENT AND TRADEMARK OFFICE
CERTIFICATE OF CORRECTION

PATENT NO.    : 6,734,294 B2
DATED         : May 11, 2004
INVENTOR(S)   : Chad C. Nelson and Lesa M. Nelson It is certified that error appears in the above-identified patent and that said Letters Patent is hereby corrected as shown below:

Column 20,
Line 3, before "sodium" remove "50 mM"
Line 4, before "zinc" remove "0.1 mM"
Line 4, after "added" insert -- (to reach 50 mM and 0.1 mM final concentrations, respectively), --
Line 15, before "sample was then" change "The" to -- To isolate nucleoside monophosphates, the --
Line 27, after "through" insert -- . --
Line 46, after "monophosphates" insert -- (dNMPs) --
Line 48, after "triphosphates" insert -- (dNTPs) --

Column 21,
Line 2, change "myokinse" to -- myokinase --
Lines 9 and 10, change "C18/SAX" to -- C18 and SAX SPE --
Line 14, before "collected" insert -- further purified and --
Line 14, after "using" change "an" to -- a ZORBAX --
Lines 15 and 16, before "Agilent Technologies" remove "ZORBAX C18 column,"
Line 18, change "(isocratic conditions)." to -- (isocratic conditions); the dNTPs in 26 mM TEABC buffer were injected in 50$\mu$L aliquots over the ZORBAX HPLC column. Peaks corresponding to the individual dNTPs were collected as a final step for purification and isolation from contaminates and minor levels of mono- and diphosphate deoxyribonucleosides (FIG. 1). After collection, the dNTPs were evaporated to dryness and azeotroped two times with 75 $\mu$L water. --
Line 20, before "column" insert -- HPLC --
Line 29, change "12C" to -- $^{12}C$ --
Lines 31-48, remove the section starting with "The purified nucleotides in a volume" and ending with "two times with 75 $\mu$L of water."
Line 39, change "FIG 1" to -- FIG. 1 --

Column 23,
Line 1, change "difference" to -- different --

Column 24,
Line 4, change "0.025" inch diameter" to -- 0.0025 inch inside diameter (ID) --
Line 15, after "conditions" insert -- : --
Line 24, change "collision" to -- collisional --

UNITED STATES PATENT AND TRADEMARK OFFICE
CERTIFICATE OF CORRECTION

PATENT NO. : 6,734,294 B2
DATED : May 11, 2004
INVENTOR(S) : Chad C. Nelson and Lesa M. Nelson It is certified that error appears in the above-identified patent and that said Letters Patent is hereby corrected as shown below:

Column 25,
Line 11, change "$^{14}$N." to -- $^{14}$N (*i.e.* purity level of isotope enrichment determined based on the mass shift of the isotopically enriched DNA molecules in the mass spectrum). --
Line 65, change "isotope compositions." to -- the broader isotope compositions for the natural-isotope molecular products compared to the isotopically-enriched products. --

Column 26,
Line 12, change "FIG. 5A" to -- FIGS. 5A --
Line 34, change "FIG. 6A" to -- FIGS. 6A --

Column 27,
Line 66, before "isotope" change "$^2$C" to -- $^{12}$C --

Column 29,
Line 8, before "enriched" change "is" to "are"
Line 12, after "enriched" insert -- in --
Line 47, before "all oxygen" insert -- wherein --

Column 32,
Line 4, change "KNA" to -- RNA --
Line 10, after "$^{16}$O" change "isotopic" to -- isotope --

Signed and Sealed this

Twenty-eighth Day of December, 2004

JON W. DUDAS
*Director of the United States Patent and Trademark Office*